United States Patent [19]

Gastinel et al.

[11] Patent Number: 5,623,053
[45] Date of Patent: Apr. 22, 1997

[54] SOLUBLE MAMMAL-DERIVED FC RECEPTOR WHICH BINDS AT A PH RANGING FROM ABOUT 5.5 TO 6.5 AND RELEASES AT A PH RANGING FROM ABOUT 7.5 TO 8.5

[75] Inventors: Louis N. Gastinel; Pamela J. Bjorkman, both of Pasadena, Calif.

[73] Assignee: California Institute of Technology, Pasadena, Calif.

[21] Appl. No.: 4,492

[22] Filed: Jan. 14, 1993

Related U.S. Application Data

[63] Continuation of Ser. No. 819,413, Jan. 10, 1992, abandoned.
[51] Int. Cl.$^6$ ............................................. C07K 14/735
[52] U.S. Cl. .......................................... 530/350; 435/69.1
[58] Field of Search ......................... 424/85.8; 435/69.1, 435/172.1; 530/350, 866, 867, 387.1; 935/10

[56] References Cited

U.S. PATENT DOCUMENTS

| | | | |
|---|---|---|---|
| 4,883,754 | 11/1989 | Boyle et al. | 435/177 |
| 4,900,660 | 2/1990 | Boyle et al. | 435/7 |
| 4,948,725 | 8/1990 | Boyle | 435/7 |
| 5,028,535 | 7/1991 | Buechler et al. | 435/7.1 |
| 5,071,756 | 12/1991 | Boyle et al. | 435/177 |
| 5,082,931 | 1/1992 | Boyle et al. | 530/413 |
| 5,085,984 | 2/1992 | Boyle et al. | 435/7.2 |

FOREIGN PATENT DOCUMENTS 8902922  4/1989  WIPO.

OTHER PUBLICATIONS

J. Alexander et al. Immunogenetics 31:169–178, 1990.
Gastinel, Louis N., et al., "Expression and Crystallization of a Soluble and Functional Form of an Fc Receptor Related to Class I Histocompatibility Molecules", Proc. Natl. Acad. Sci. U.S.A., vol. 89, pp. 638–642, Jan. 15, 1992. Note: Publication after Filing Date of present patent application.
Madden, D.R., et al. "The Structure of HLA–B27 Reveals Nonamer Self–Peptides Bound in an Extended Conformation", Nature, vol. 353, pp. 321–325, Oct. 15, 1991.
Schumacher, Ton N.M., et al. "Direct Binding of Peptide to Empty MHC Class I Molecules on Intact Cells and In Vitro", Cell, vol. 62, pp. 563–567, Aug. 10, 1990.
Lin, A.Y., et al. "Expression of T Cell Antigen Receptor Heterodimers in a Lipid–Linked Form", Science, vol. 249, pp. 677–679, Aug. 10, 1990.
Townsend, A., et al. "Assembly of MHC Class I Molecules Analyzed in Vitro", Cell, vol. 62, pp. 285–295, Jul. 27, 1990.
Johnson, W. Curtis, Jr., "Protein Secondary Structure and Circular Dichroism: A Practical Guide", Proteins: Structure, Function, and Genetics, vol. 7, pp. 205–214, 1990.
McKnight, James C., "Functional and Nonfunctional LamB Signal Sequences Can Be Distinguished by Their Biophysical Properties", The Journal of Biological Chemistry, vol. 264, No. 29, pp. 17293–17297, Oct. 15, 1989.

Townsend, Alain, et al., "Association of Class I Major Histocompatibility Heavy and Light Chains Induced by Viral Peptides" Nature, vol. 340, pp. 443–448, Aug. 10, 1989.
Simister, N.E. et al., "Cloning and Expression of the Neonatal Rat Intestinal Fc Receptor, a Major Histocompatibility Complex Class I Antigen Homolog", Cold Spring Harbor Symposia on Quantitative Biology, vol. LIV, pp. 571–580, Jul. 1989.
Gorga, Joan C. et al., "Comparison of the Secondary Structures of Human Class I and Class I Major Histocompatibility Complex Antigens by Fourier Transform Infrared and Circular Dichroism Spectroscopy", Proc. Natl. Acad. Sci. U.S.A., vol. 86, pp. 2321–2325, Apr. 1989.
Simister, N.E. et al., "An Fc Receptor Structurally Related to MHC Class I Antigens", Nature, vol. 337, pp. 184–187, Jan. 12, 1989.
Sundelin, J., et al., "The Complete Amino Acid Sequence of Rat $\beta_2$–Microglobulin" Scand. J. Immunol., vol. 27, pp. 195–199, 1988.
Takebe, Yutaka, et al., "SRα Promoter: an Efficient and Versatile Mammalian cDNA Expression System Composed of the Simian Virus 40 Early Promoter and the R–U5 Segment of Human T–Cell Leukemia Virus, Type I Long Terminal Repeat", Molecular and Cellular Biology, vol. 8, No. 1, pp. 466–472, Jan. 1988.
Caras, Ingrid W., et al., "Signal for Attachment of a Phospholipid Membrane Anchor in Decay Accelerating Factor", Science, vol. 238, pp. 1280–1283, Nov. 27, 1987.

(List continued on next page.)

*Primary Examiner*—John Ulm
*Assistant Examiner*—Lorraine Spector
*Attorney, Agent, or Firm*—Shirley L Church

[57] ABSTRACT

The present invention pertains to a new composition of matter in the form of a soluble Fc receptor (pHsFcR) is created. The pHsFcR has a pH–determinable binding capability for at least one antibody or complex thereof. The pHsFcR is produced using the cDNA for a transmembrane, pH–determinable Fc receptor found in nature which has the capability of binding to at least one antibody or complex thereof. The most preferred embodiment of the present invention is a secreted form of pHsFcR which is produced using a modified cDNA of the transmembrane Fc receptor; the modified cDNA is obtained by the creation of a new in-frame stop codon and the deletion of the DNA sequence encoding the transmembrane (and typically the cytoplasmic) domain of the transmembrane Fc receptor. This creates a new gene that encodes a completely soluble protein consisting of the extracellular domains of the transmembrane Fc receptor. The new gene is used in formation of an expression vector which is introduced into a procaryotic or eucaryotic cell, followed by selection for a procaryotic or eucaryotic cell comprising the modified cDNA of the desired secreted pHsFcR. The selected cells are grown, during which pHsFcR is secreted into the growth medium. The secreted pHsFcR can then be separated from the growth medium using an affinity column comprising an antibody to which the pHsFcR can bind.

7 Claims, 8 Drawing Sheets

OTHER PUBLICATIONS

Bjorkman, P.J., et al., "Structure of the Human Class I Histocompatibility Antigen, HLA–A2", Nature, vol. 329, pp. 506–512, Oct. 8, 1987.

Matsudaira, Paul, "Sequence from Picomole Quantities of Proteins Electroblotted Onto Polyvinylidine Difluoride Membranes", The Journal of Biological Chemistry, vol. 262, pp. 10035–10038, Jul. 1987.

Kunkel, Thomas A. et al., "Rapid and Efficient Site–Specific Mutagenesis Without Phenotypic Selection", Methods in Enzymology, vol. 154, pp. 367–383, 1987.

Bebbington & Hentschel, "DNA Cloning" ed. Glover IRL. Oxford Press 1987, Chapter 8, pp. 163–188, Entitled: The Use of Vectors Based on Gene Amplification for Expression of Cloned genes in Mammalian Cells, 1987.

Simister, Neil E,. et al., "Isolation and Characterization of an Fc Receptor from Neonatal Rat Small Intestine", Eur. J. Immunol., vol. 15, pp. 733–738, 1985.

Yokoyama, Kazushige, et al., "Secondary Structure of the Murine Histocompatibility Alloantigen H–2K$^b$ Relationship between Heavy Chain, $\beta_2$–Microglobulin, and Antigenic Reactivity", Biochemistry, vol. 24, pp. 3002–3006, 1985.

Bernabeu, Carmelo, et al., "$\beta_2$–Microglobulin from Serum Associates with MCH Class I Antigens on the Surface of Cultured Cells", Nature, vol. 308, pp. 642–645, Apr. 1984.

Groves, Merton L., et al., "Complete Amino Acid Sequence of Bovine $\beta_2$–Microglobulin", The Journal of Biological Chemistry, vol. 257, No. 5, pp. 2619–2626, Mar. 10, 1982.

Parham, Peter, "Purification of Immunologically Active HLA–A and –B Antigens by a Series of Monoclonal Antibody Columns", The Journal of Biological Chemistry, vol. 254, No. 18, pp. 8709–8712, Sep. 25, 1979.

Lancet, Doron, et al., "Heavy Chain of HLA–A and HLA–B Antigens in Conformationally Labile: A Possible Role for $\beta_2$–Microglobulin", Proc. Natl. Acad. Sci., U.S.A., vol. 76, No. 8, pp. 3844–3848, Aug. 1979.

Greenfield, Norma, et al., "Computed Circular Dichroism Spectra for the Evaluation of Protein Conformation", Biochemistry, vol. 8, No. 10, pp. 4108–4116, Oct. 1969.

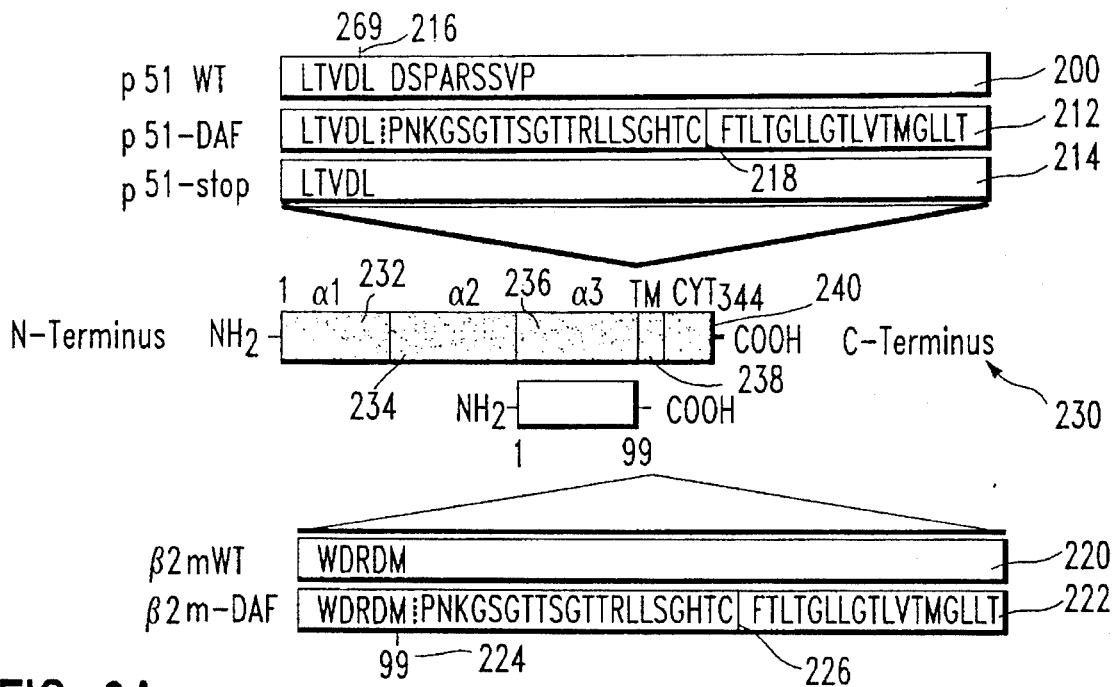
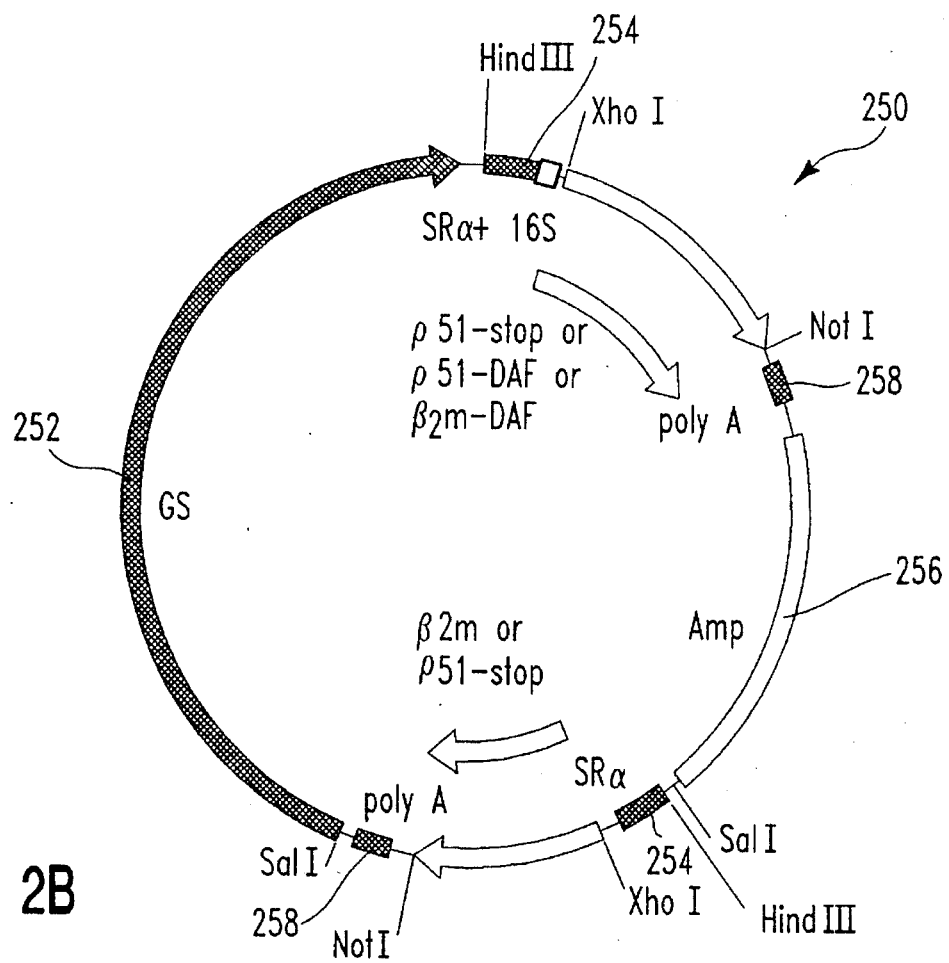
FIG. 2A
FIG. 2B pBJ₁ pSVLGS.1' pBJ5-GS/p51-DAF pBJ1/β2m pBJ5-GS/β2m-DAF pBJ1/p51-stop pBJ5-GS/p51-stop

SOLUBLE MAMMAL-DERIVED FC RECEPTOR WHICH BINDS AT A PH RANGING FROM ABOUT 5.5 TO 6.5 AND RELEASES AT A PH RANGING FROM ABOUT 7.5 TO 8.5

This application is a Continuation of prior U.S. application Ser. No. 07/819,413 filing Date Jan. 10, 1992, now abandoned.

BACKGROUND OF THE INVENTION

1. Field of the Invention

The present invention relates to a soluble Fc receptor and a method for its production.

2. Description of the Background Art

Immunoglobulins, also referred to as antibodies, are a major component of the humoral immune response of all mammals. These glycoproteins are divided into five major structural classes, each of which can be divided into subclasses. The five major classes are IgA, IgD, IgE, IgG, and IgM. IgG is the most common class of immunoglobulins found in the serum.

It is the highly specific interaction between an antibody and its target antigen that makes an immunoglobulin an effective agent against an invading pathogen. The high specificity of the immunoglobulin—antigen interaction allows the immune system to attack the foreign antigen with minimal harm to the host organism° In general, immunoglobulins have a high affinity for their target antigen with an average dissociation constant (Kd) for the antigen—antibody complex on the order of $10^{-9}$ to $10^{-12}$ moles/liter.

Immunoglobulins are composed of four polypeptide chains; two identical light chains, each of approximately 25 kD in molecular mass and two identical heavy chains, each of approximately 50–80 kD in molecular mass. The different classes of antibodies are distinguished by structural differences in their heavy chains. A schematic drawing of an IgG 10 is shown in FIG. 1.

Light chains 12 and 14 have been characterized as having a single amino terminal variable domain (a domain is a distinct region of tertiary protein structure), $V_L$ and a single constant domain, $C_L$. The term variable refers to the variability in amino acid sequence found in this type of domain between antibodies with different antigen binding specificities, which antibodies are of the same immunoglobulin class and subclass. The heavy chains 16 and 18 of an IgG contain a single amino terminal variable domain, VH, followed by three constant domains, $C_H1$, $C_H2$, and $C_H3$, as shown in FIG. 1.

In general, an immunoglobulin, and in particular IgG, may be characterized as a Y shaped molecule in which each upper arm of the Y is formed by a pairing of a single light chain ($V_L+C_L$) with the two most amino terminal domains of a single heavy chain ($V_H+C_{H1}$). It is the pairing of the variable domains of the light and heavy chains that forms the antigen binding sites 20 and 22. The constant domain of the light chain ($C_L$) interacts with the first constant domain of the heavy chain .($C_H1$). The heavy and light chains are covalently bound to each other by a disulfide bond 24 between the paired $C_L$ and $C_H1$ domains. The two heavy chains dimerize through interactions between their 2nd and 3rd constant domains ($C_H2$ and $C_H3$). The two heavy chains are also covalently bound to each other through interchain disulfide bonds 26. These disulfide bonds 26 connect the two heavy chains in a region between the $C_H1$ and $C_H2$ domains that is known as the hinge region. Beneath the hinge region are oligosaccharide units (carbohydrates) 28 and 30, which are attached to the $C_H2$ domains within the structure. The $V_L$ and $C_L$ of the light chain paired with $V_H$ and $C_H1$ of the heavy chain is called an Fab, FIG. 1 at 32 and 34; and, the paired $C_H2$ and $C_H3$ domains of the IgG heavy chains is referred to as the Fc, FIG. 1 at 36, of the antibody.

Typically, immunoglobulin molecules are soluble in aqueous solution and bind to compounds in a highly specific manner with a great affinity. It is possible to produce antibodies against virtually any organic compound known to humans. These characteristics of immunoglobulins have resulted in their widespread analytical and therapeutic use throughout the biological sciences.

Fc receptor is a general term that refers to any one of several proteins that bind to the Fc region of an immunoglobulin. Fc receptors can be soluble or membrane-bound. An example of a membrane-bound Fc receptor is the FcRn from the intestines of neonatal rats. The FcRn was recently cloned and characterized by N. E. Simister and K. E. Mostov, as described in "An Fc Receptor Structurally Related to MHC Class I Antigens" Nature (London) Vol. 337, pp. 184–187 (1989).

| Met -22 | Gly | Met -20 | Ser | Gln | Pro | Gly | Val -15 | Leu | Leu | Ser | Leu | Leu -10 | Leu | Val | Leu |
|---|---|---|---|---|---|---|---|---|---|---|---|---|---|---|---|
| Leu | Pro -5 | Gln | Thr | Trp | Gly -1 | Ala +1 | Glu | Pro | Arg | Leu 5 | Pro | leu | Met | Tyr | His 10 |
| Leu | Ala | Ala | Val | Ser 15 | Asp | Leu | Ser | Thr | Gly 20 | Leu | Pro | Ser | Phe 25 | Trp | Ala |
| Thr | Gly | Trp | Leu 30 | Gly | Ala | Gln | Gln | Tyr 35 | Leu | Thr | Tyr | Asn | Asn 40 | Leu | Arg |
| Gln | Glu | Ala 45 | Asp | Pro | Cys | Gly | Ala 50 | Trp | Ile | Trp | Glu | Asn 55 | Gln | Val | Ser |
| Trp | Tyr 60 | Trp | Glu | Lys | Glu | Thr 65 | Thr | Asp | Leu | Lys | Ser 70 | Lys | Glu | Gln | Leu |
| Phe 75 | Leu | Glu | Ala | Ile | Arg 80 | Thr | Leu | Glu | Asn | Gln 85 | Ile | Asn | Gly | Thr | Phe 90 |
| Thr | Leu | Gln | Gly | Leu 95 | Leu | Gly | Cys | Glu | Leu 100 | Ala | Pro | Asp | asn | Ser 105 | Ser |
| Leu | Pro | Thr | Ala 110 | Val | Phe | Ala | Leu | Asn 115 | Gly | Glu | Glu | Phe | Met 120 | Arg | Phe |
| Asn | Pro | Arg 125 | Thr | Gly | Asn | Trp | Ser 130 | Gly | Glu | Trp | Pro | Glu 135 | Thr | Asp | Ile |
| Val | Gly 140 | Asn | Leu | Trp | Met | Lys 145 | Gln | Pro | Glu | Ala | Ala 150 | Arg | Lys | Glu | Ser |

-continued

| | | | | | | | | | | | | | | |
|---|---|---|---|---|---|---|---|---|---|---|---|---|---|---|
| Glu 155 | Phe | Leu | Leu | Thr | Ser 160 | Cys | Pro | Glu | Arg | Leu 165 | Leu | Gly | His | Leu | Glu 170 |
| Arg | Gly | Arg | Gln | Asn 175 | Leu | Glu | Trp | Lys | Glu 180 | Pro | Pro | Ser | Met | Arg 185 | Leu |
| Lys | Ala | Arg | Pro 190 | Gly | asn | Ser | Gly | Ser 195 | Ser | Val | Leu | Thr | Cys 200 | Ala | Ala |
| Phe | Ser | Phe 205 | Tyr | Pro | Pro | Glu | Leu 210 | Lys | Phe | Arg | Phe | Leu 215 | Arg | Asn | Gly |
| Leu | Ala 220 | Ser | Gly | Ser | Gly | Asn 225 | Cys | Ser | Thr | Gly | Pro 230 | Asn | Gly | Asp | Gly |
| Ser 235 | Phe | His | Ala | Trp | Ser 240 | Leu | Leu | Glu | Val | Lys 245 | Arg | Gly | Asp | Glu | His 250 |
| His | Tyr | Gln | Cys | Gln 255 | Val | Glu | His | Glu | Gly 260 | Leu | Ala | Gln | Pro | Leu 265 | Thr |
| Val | Asp | Leu | Asp 270 | Ser | Pro | Ala | Arg | Ser 275 | Ser | Val | Pro | Val | Val 280 | Gly | Ile |
| Ile | Leu | Gly 285 | Leu | Leu | Leu | Val | Val 290 | Val | Ala | Ile | Ala | Gly 295 | Gly | Val | Leu |
| Leu | Trp 300 | Asn | Arg | Met | Arg | Ser 305 | Gly | Leu | Pro | Ala | Pro 310 | Trp | Leu | Ser | Leu |
| Ser 315 | Gly | Asp | Asp | Ser | Gly 320 | Asp | Leu | Leu | Pro | Gly 325 | Gly | Asn | Leu | Pro | Pro 330 |
| Glu | Ala | Glu | Pro | Gln 335 | Gly | Val | Asn | Ala | Phe 340 | Pro | Ala | Thr | Ser. 344 | | |

This Fc receptor (FcRn) is physiologically expressed on the luminal surface of neonatal rat intestinal epithelial cells. The FcRn was determined to optimally bind to IgG at the intestinal pH of 6–6.5 and to release bound IgG at the serosal pH of approximately 7.5. The physiological role of FcRn is to bind to maternal IgG consumed by the newborn when it drinks its mother's milk. The FcRn is then involved in the transport of the bound IgG across the intestinal epithelial barrier and the release of the IgG into the blood of the newborn. By this means the neonatal rat can passively acquire some resistance to disease. This is especially important during the first few weeks of independent life of the rat (as well as the cat) because at birth these mammals are practically agammaglobulinemic (without antibodies). FcRn, as found on the surface of neonatal rat intestinal epithelial cells, is a heterodimer consisting of an FcRn heavy chain (p51) of approximately 45–53 kD in molecular mass and a light chain ($\beta_2$m) of approximately 14 kD in molecular mass. The FcRn heavy chain appears to have 3 extracellular domains, a transmembrane domain and a cytoplasmic tail. The three extracellular domains of the FcRn heavy chain have significant sequence similarity to the corresponding domains of Class I Major Histocompatibility Complex (MHC) molecules. This sequence similarity suggests that the FcRn may have a tertiary protein structure similar to that observed for Class I MHC molecules. The FcRn light chain is a $\beta_2$m ($\beta$-2 microglobulin), a soluble single domain protein also found as a component of the Class I MHC molecule heterodimer.

The sequence for rat $\beta_2$m was published by J. Sundelin et al. Scand. J. Immunol. 27, pp. 195–199 (1988) as follows:

| | | | | | | | | | | | | | | |
|---|---|---|---|---|---|---|---|---|---|---|---|---|---|---|
| Ile 1 | Gln | Lys | Thr | Pro 5 | Gln | Ile | Gln | Val | Tyr 10 | Ser | Arg | His | Pro | Pro 15 | Glu |
| Asn | Gly | Lys | Pro 20 | Asn | Phe | Leu | Asn | Cys 25 | Tyr | Val | Ser | Gln | Phe 30 | His | Pro |
| Pro | Gln | Ile 35 | Glu | Ile | Glu | Leu | Leu 40 | Lys | Asn | Gly | Lys | Lys 45 | Ile | Pro | Asn |
| Ile | Glu 50 | Met | Ser | Asp | Leu | Ser 55 | Phe | Ser | Lys | asp | Trp 60 | Ser | Phe | Tyr | Ile |
| Leu 65 | Ala | His | Thr | Glu | Phe 70 | Thr | Pro | Thr | Glu | Thr 75 | Asp | Val | Tyr | Ala | Cys 80 |
| Arg | Val | Lys | His | Val 85 | Thr | Lys | Leu | Glu | Pro 90 | Lys | Thr | Val | Thr | Trp 95 | Asp |
| Arg | Asp | Met. 99 | | | | | | | | | | | | | |

The transmembrane domain of the FcRn heavy chain anchors the FcRn heterodimer into the cell membrane of the intestinal epithelial cells. The hydrophobic nature of this transmembrane domain precludes the solubilization of this protein in an aqueous buffer in the absence of surfactants, which are often toxic, which can reduce the stability of proteins, and which are often difficult to remove once they have been in contact with the protein.

There are numerous potential applications for an Fc receptor which is soluble in aqueous solutions without the use of a surfactant. In addition, an Fc receptor, such as the FcRn, which is capable of binding antibodies at one pH and releasing the antibodies at another, is one that could be used in the biotechnology industry. Fc receptors can be used in medicine for the detection of antibodies under conditions of physiological pH. In addition, in U.S. patent application, Ser. No. 07/819,040, of Andrew Huber et al., filed Jan. 10, 1992, it is disclosed that soluble FcRn receptors of the kind disclosed and claimed herein can be attached to a surface and used to concentrate and purify antibodies from mixtures comprising antibodies such as IgG from blood, ascites or tissue culture supernatants (growth medium in which cells are cultured).

However, the usefulness of the membrane-bound FcRn is limited by the fact that, like other transmembrane proteins, it is not readily soluble in an aqueous solution in the absence of surfactants, as described above.

Although cDNA for the membrane-bound FcRn was available from N. E. Simister, it was questionable whether a soluble FcRn could be produced. The soluble FcRn, like other proteins must be able to fold into a functional three dimensional structure. This folding of a protein in solution is a very complex process and is influenced by many factors, such as the presence of other proteins which assist in the folding process. Upon removal of the transmembrane domain from the FcRn, the resultant protein might not be able to fold properly in solution, rendering it non-functional and probably insoluble. Even if the protein were able to fold properly, it might not be secreted from the cell in which it is produced and/or it might simply be degraded within the cell. Further, depending on where the heavy chain of FcRn is truncated to remove the transmembrane domain, the truncated heavy chain might be less heat stable and might not associate with its intended light chain, which would affect its ability to bind to an antibody.

Definitions

The following definitions are for use in understanding the descriptions presented throughout the present application.

FcRn is understood to mean rat neonatal, intestinal, pH-determinable membrane-bound Fc receptor(s);

pHsFcRn is understood to mean a soluble form of FcRn produced by applicants;

pHFcR is understood to mean a membrane-bound fc receptor having the ability to bind to an antibody monomer or complex thereof at one pH and to release the antibody or complex thereof at another pH;

sFcR is understood to mean soluble, vertebrated-derived Fc receptor in general;

pHsFcR is understood to mean soluble, vertebrate-derived Fc receptor having the ability to bind to an antibody monomer or complex thereof at one pH and to release the antibody or complex thereof at another pH;

αMEM is understood to mean a commercially available growth medium supplied by Irvine Scientific and Gibco/BRL;

$\beta_2$m is understood to mean $\beta_2$-microglobulin;

cDNA is understood to mean complementary DNA prepared from mRNA.

DAF is understood to mean decay-accelerating factor;

DMEM is understood to mean a commercially available growth medium supplied by Irvine Scientific and Gibco/BRL;

MHC is understood to mean major histocompatibility complex;

MSX is understood to mean L-methionine sulfoximine; and

PI-PLC is understood to mean phosphatidylinositol—specific phospholipase C;

SUMMARY OF THE INVENTION

In accordance with the present invention, a new composition of matter in the form of a soluble vertebrate-derived Fc receptor (pHsFcR) has been created. The pHsFcR has a pH-determinable binding capability for at least one antibody monomer or complex thereof. The pHsFcR was produced using the cDNA of a transmembrane, pH-determinable, vertebrate-derived Fc receptor found in nature that is capable of binding to at least one antibody monomer or complex thereof. The pHsFcR of the present invention can be produced by removing the amino acid residues responsible for the attachment of the pHFcR to the cell membrane. In the case of secreted pHsFcR, this is accomplished at the DNA level by eliminating the DNA that encodes the transmembrane domain(s) of the protein. In the case of lipid-linked pHFcR, a pHsFcR can be generated at the protein level by cleaving the protein polypeptide chain between the desired extracellular domains and the amino acids responsible for the attachment of the protein to the cell membrane.

The secreted pHsFcR was produced from the transmembrane Fc receptor cDNA by the creation of a new in-frame stop codon and the deletion of the DNA sequence encoding the transmembrane (and typically the cytoplasmic) domain of the transmembrane protein. The new gene thereby created encoded a completely soluble protein consisting of the extracellular domains of the vertebrate-derived transmembrane protein. In the preferred embodiment of the secreted pHsFcR, the cDNA sequence encoding the transmembrane and cytoplasmic domains of an FcRn heavy chain was deleted from the FcRn cDNA. Specifically, a modified heavy chain cDNA fragment was produced by inserting a stop codon after the codon for amino acid 269 in the full length heavy chain cDNA for FcRn. The amino acid 269 position is shown in FIG. 2A for FcRn heavy chain (p51 WT). The full amino acid sequence for FeRn heavy chain, including the FcRn cDNA, is provided in the N. E. Simister and K. E. Mostov paper referenced previously (Nature, 337, pp. 184–187, 1989). The position selected for insertion of the stop codon (after the codon for amino acid 269) was based on similarities between the heavy chain subunit, p51, of FcRn and the corresponding domains of the Class I MHC proteins, wherein the last residue of the Class I α3 domain is residue 274. The FcRn heavy chain cDNA fragment described above was used to produce a truncated heavy chain of the FcRn, which associated with a β2m light chain to produce a soluble FcRn (pHsFcRn). The full amino acid sequence for $\beta_2$m light chain is provided in a paper by J. Sundelin et al., "The Complete Amino Acid Sequence of Rat $\beta_2$-microglobulin", Scand. J. Immunol., Vol. 27, pp. 195–199 (1988).

The FcRn heavy chain amino acid 269 position is probably not the only position at which truncation is possible. Because the histidine amino acids of the alpha 3 domain are probably involved in the binding of the Fc of IgG, the position of truncation has to preserve these amino acids as part of the alpha 3 domain. In the alpha 3 domain, there are 4 histidine residues which are located at sequence positions 237, 250, 251 and 258. Studies in the laboratory, are in progress to establish the exact role of these residues in the Fc binding property of pHsFCRn. However, applicants believe that a truncation within the amino acid range of about 260 to 280 will produce a suitable truncated FcRn heavy chain.

Because the alpha 3 domain of mHC Class I molecules interacts principally with $\beta_2$m, and FcRn appears to be structurally analogous to Class I MHC molecules, the alpha 3 domain of FcRn probably binds to $\beta_2$m also. The functionality of FcRn heavy chain appears to be dependent upon the presence of an associated $\beta_2$m. Thus, the functionality of the Fc receptor may be lost if the alpha 3 domain is deleted.

The pHsFcRn was tested and found to have maintained its ability to bind to antibodies. In addition, as described in U.S. patent application, Ser. No. 07/819,040 which was filed simultaneously with the present patent application, it is possible to attach the above-described pHsFcRn of the present invention to a surface and to use the attached, immobilized pHsFcRn to concentrate, isolate or purify antibodies from a mixture comprising such antibodies.

In the specific embodiments of the present invention, the cDNAs for the heavy and light chains of membrane-bound FcRn were used as the starting materials to produce the pHsFcRn. However, one skilled in the art, in view of the present disclosure, should be able to produce a soluble form of a different, membrane-bound Fc receptor, providing it has adequate similarity in the heavy chain domains. For example, the present method can be used to produce pH dependent, soluble Fc receptors from vertebrate (and particularly mammalian) transmembrane Fc receptors homologous to FcRn.

In the specific embodiments of the present invention the expression vectors, as illustrated in FIG. 2B, contained the glutamine synthetase gene which confers resistance to L-methionine sulfoximine. (The CellTech glutamine synthetase-based selection/amplification gene was used to produce the desired expression vectors.) However, other selection/amplification genes can be expected to perform well also, such as the DHFR (dihydrofolate reductase) gene, which confers resistance to methotrexate. This latter gene is commonly used for protein expression (selection & amplification).

In the specific embodiments of the present invention, the expression of the lipid-linked forms of FcRn and the secreted sFcRn was carried out using CHO cells (eukaryotic cells). However, since it has presently been discovered that the carbohydrate component of the Fc receptor is not involved in Fc binding, the bacterial production (prokaryotic cells) of lipid-linked pHFcR and secreted pHsFcR is expected to be feasible.

Applicants believe expression of the lipid-linked pHFcR and secreted pHsFcR of the present invention can be carried out in Eukaryotic cells such as CHO cells, Rat2 cells, and 3T3 (mouse cell line), for example and not by way of limitation.

When the sFcR is to be used to concentrate or purify antibodies from mixtures comprising the antibodies, it is desirable that the technique for concentration or purification be a gentle one. In the case of a physiological pHsFcRn, the receptor binds to the Fc portion of antibodies at a pH ranging from about 6.0 to about 6.5, and releases the antibodies at a pH ranging from about 7.5 to about 8.0. A process operable over this pH range is most preferred, since it does not affect the antibody molecule in a manner which affects its normal performance as an antibody. The preferred pHsFcR of the present invention are those which can bind to the Fc portion of at least one kind of immunoglobulin (antibody) at a pH ranging from about 5.5 to about 6.5 and can release the Fc portion of the immunoglobulin at a pH ranging from about 7.5 to about 8.5. In general, the pHsFcR of the present invention are those which can both bind to and release from the Fc portion of the antibody over a pH ranging from about 4 to about 9. The pHsFcR may bind to the antibody at a given pH and release at a higher pH or may bind at a given pH and release at a lower pH.

A method of producing the vertebrate-derived pHsFcR of the present invention comprises the following steps:

(a) creating a gene fragment for a truncated heavy chain of the desired vertebrate-derived pHsFcR, said fragment excluding the transmembrane domain of said heavy chain;

(b) forming an expression vector comprising a gene useful as a selectable marker and optionally a means of gene amplification, the pHsFcR heavy chain gene fragment from step (a), and a gene fragment for the light chain compatible with the pHsFcR heavy chain gene fragment of step (a);

(c) introducing the expression vector of step (b) into a procaryotic or eucaryotic cell;

(d) selecting for a procaryotic or eucaryotic cell comprising the modified and optionally amplified cDNAs of the desired vertebrate-derived pHsFcR;

(e) growing the cell of step (d), from which the desired pHsFcR is harvested.

The pHsFcR is typically secreted from the cell of step (d) into the growth medium during the growing process of step (e); however, when secretion does not occur, it may be necessary to carry out an additional step (f): lysing the cells grown in step (e), whereby the pHsFcR is released from the cells.

An alternative method of producing the vertebrate-derived pHsFcR receptor of the present invention pertains to production of a lipid-linked pHFcR, wherein the lipid linkage is cleaved, thereby releasing a pHsFcR; this method comprises the following steps:

(a) creating a gene fragment comprising a vertebrate-derived Fc receptor truncated heavy chain, the fragment excluding the transmembrane domain of the heavy chain but including a signal specifying the attachment of a lipid;

(b) forming an expression vector comprising a gene useful as a selectable marker and optionally a means of gene amplification, the step (a) heavy chain gene fragment including the lipid attachment signal, and a gene fragment for the light chain compatible with the pHFcR heavy chain gene fragment of step (a);

(c) introducing the expression vector of step (b) into a procaryotic or eucaryotic cell;

(d) selecting a procaryotic or eucaryotic cell comprising the modified and optionally amplified cDNA of the desired vertebrate-derived pHFcR;

(e) growing the cell of step (d) from which the desired pHFcR is obtained;

(f) cleaving the pHFcR lipid linkage of the step (d) cell membrane to produce a pHsFcR.

The above-described method for production of a pHsFcR from a lipid-linked pHFcR can also be carried out wherein the signal for attachment of a lipid is included in the gene fragment of the light chain and wherein the gene fragment for the truncated heavy chain has been constructed to delete the DNA sequence encoding the transmembrane domain of the transmembrane protein from which it was derived.

An additional step will typically be used with the three above-described methods, wherein:

separation of the pHsFcR from a growth medium or other solution containing contaminating proteins is achieved using an affinity column comprising an antibody to which the pHsFcR can bind.

Typically the compatible light chain used in combination with the truncated heavy chain derived from the membrane-bound Fc receptor is a $\beta_2$ microglobulin ($\beta_2$m).

The gene fragment for the heavy chain of the desired pHsFcR or pHFcR can be introduced into the procaryotic or eucaryotic cell for amplification in the same expression vector with the gene fragment for the light chain compatible with the heavy chain, as described above. It is also possible to introduce the gene fragment for the heavy chain and the gene fragment for the compatible light chain into the procaryotic or eucaryotic cell in separate expression vectors, so long as the selection and optionally, amplification process within the cell is not materially affected.

BRIEF DESCRIPTION OF THE DRAWINGS

FIG. 2A shows a schematic diagram of the primary structures of the normal FcRn heavy chain as found in nature (p51 wild type, p51 WT)(SEQ. I.D. NO. 3) 200; and rat $\beta_2$m as found in nature ($\beta_2$m wild type, $\beta_2$m WT)(SEQ. I.D. NO. 6) 220; and novel proteins in which: the lipid-attachment sequence from DAF was fused to an FcRn heavy chain truncated at residue 269 (p51-DAF)(SEQ. I.D. NO. 4) 212; the lipid-attachment sequence from DAF was fused to the C terminus of $\beta_2$m wild type ($\beta_2$m-DAF) 222; or, in which a stop codon was introduced into FcRn heavy chain after residue 269 (p51 stop)(SEQ. I.D. NO. 5) 214. The mature transmembrane-bound FcRn heavy chain 230 consists of three extracellular domains ($\alpha$1 232, $\alpha$2 234, and $\alpha$3 236) with sequence similarity to the corresponding domains of Class I MHC molecules, and an unrelated transmembrane (TM) 238 and cytoplasmic (CYT) region 240. The lipid attachment signal from DAF, as described by I. W. Caras et at., Science, Vol.23, pp. 1280–1283 (1987), (as residues 311–347) was fused following residue 269 (as shown in FIG. 2A at 216) of the FcRn heavy chain 200 to form p51-DAF 212, or following the final amino acid (residue 99) (as shown in FIG. 2A at 224) of $\beta_2$m 220 to form $\beta_2$m-DAF (SEQ. I.D. NO. 7) 222. Residues N-terminal of the solid vertical line (FIG. 2A at 218 and 226)are retained in the chimeric fusion proteins.

FIG. 2B shows a schematic diagram of the triple expression vectors 250 used to transfect CHO cells and express the proteins. Illustrated are: GS, glutamine synthetase gene 252; SR$\alpha$, promoter used to regulate transcription of downstream cDNAs 254; poly A addition signal 258; and Amp, ampicillin-resistance gene 256. Arrows indicate orientation of cDNA relative to the GS minigene. Three expression vectors were created: pBJ5-GS/p51-DAF/$\beta_2$m, to express PI-linked FcRn heavy chain with soluble $\beta_2$m; pBJ5-GS/p51-stop/$\beta_2$m-DAF, to express truncated (soluble) FcRn heavy chain with PI-linked $\beta_2$m; and pBJ5-GS/p51-stop/$\beta_2$m, to express secreted heterodimer.

DETAILED DESCRIPTION OF THE PREFERRED EMBODIMENT

Figure 1:
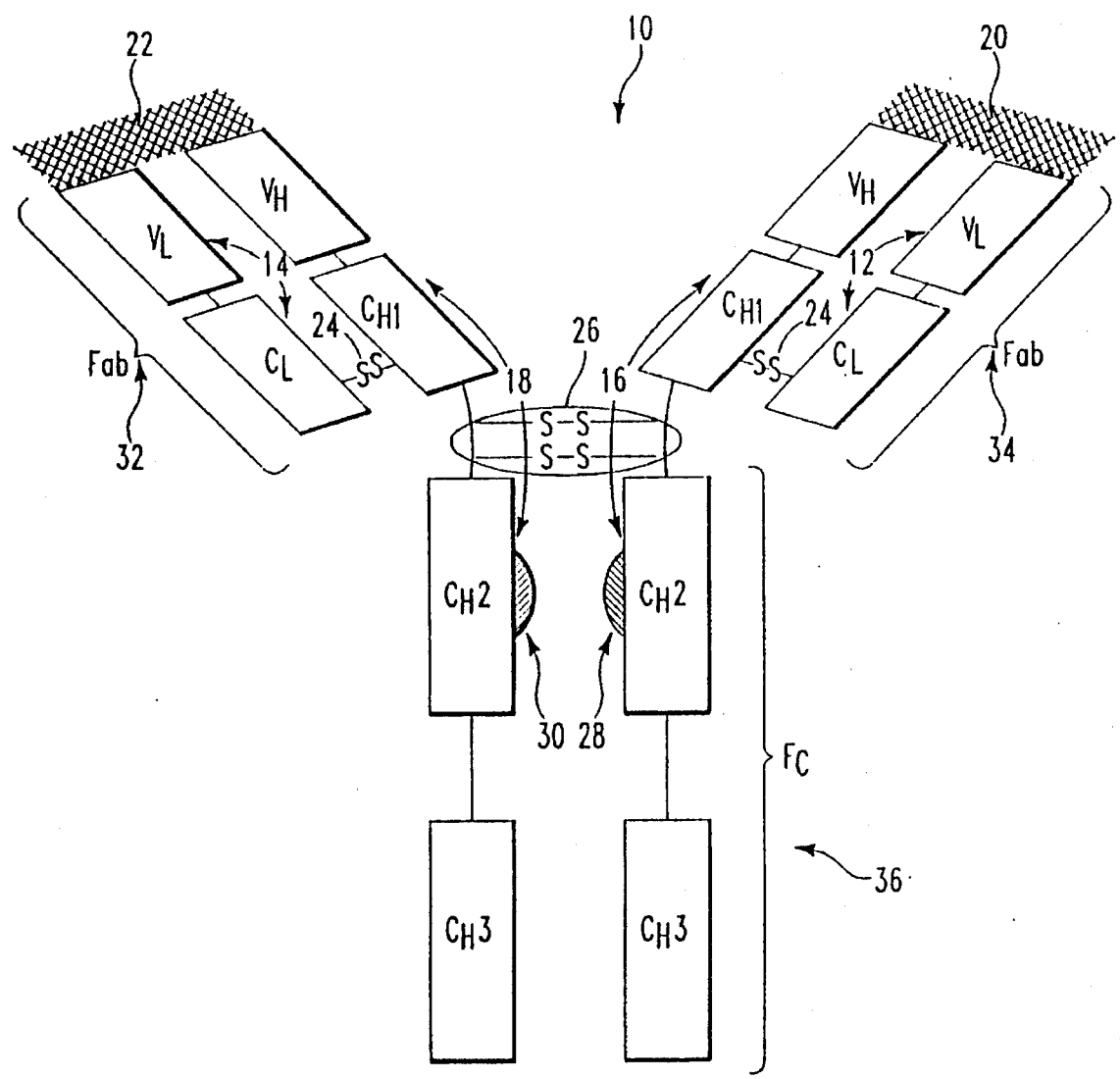
FIG. 1 shows a schematic drawing of an IgG molecule.

The present invention pertains to a composition of matter comprising a soluble, vertebrate-derived Fc receptor having a pH-determinable capability for binding to the Fc portion of an antibody monomer or a complex thereof, this composition has been named a pHsFcR herein. The invention also pertains to a method of producing a pHsFcR, since, in the known art, Fc receptors which have a pH-determinable capability for binding to the Fc portion of an antibody monomer or a complex thereof are membrane-bound (transmembrane proteins). The ability of the pHsFcR of the present invention to bind to antibodies in a pH-determinable (pH-dependent) manner is not affected upon rendering the membrane-bound Fc receptor soluble by the method of the present invention.

The pHsFcR of the present invention can be produced by removing the amino acid residues responsible for the attachment of the pHFcR to the cell membrane. In the case of secreted pHsFcR this is accomplished at the DNA level by eliminating the DNA that encodes the transmembrane domain(s) of the protein. In the case of lipid-linked pHFcR, a pHsFcR can be generated at the protein level by cleaving the protein polypeptide chain between the desired extracellular domains and the amino acids responsible for the attachment of the protein to the cell membrane.

Due to the complexity of macromolecules and their interactions in general, it was necessary for the applicants to use the cDNA of an existing, pH-determinable, membrane-bound Fc receptor molecule as the starting material in the method of producing the soluble Fc receptor of the present invention. However, a strategy for secretion of a normally-membrane-bound heterodimeric glycoprotein by deletion of the transmembrane region has not always been successful.

Applicants decided to use the cDNA from rat Fc receptor, FcRn, as the starting material of the preferred embodiment.

Deletion of the transmembrane region of the FcRn was attempted through introduction of an in-phase translation stop codon. Due to the uncertainty involved, prior to construction of a secreted pHsFcRn, two different lipid-linked forms of FcRn (pHFcR) were constructed which were likely to be solubilized by treatment with PI-PLC to generate pHsFcRn. Subsequently, a cell line that secreted a pHsFcR was developed.

The first form of lipid-linked FcRn was produced by constructing a modified FcRn heavy chain in which amino acid residue 269 was followed by the lipid-anchoring signal from DAF. The lipid-anchoring signal from DAF is shown in FIG. 2A attached to the C-terminus of the truncated p 51 at 212 and attached to the C-terminus of $\beta_2$-m at 222. This portion of the FcRn was expressed together with rat $\beta_2$m in CHO cells using a glutamine synthetase-based amplifiable expression system. (Residue 269 is the counterpart of the human MHC-Class I residue 274, which is the last residue of the class I $\alpha$3 domain.)

The second lipid-linked form of FcRn was produced by constructing a modified rat $\beta_2$m in which its C Terminal residue was followed by the lipid-anchoring signal from DAF. This portion of the FcRn was expressed together with a heavy chain truncated after residue 269.

Figures 11, 12:
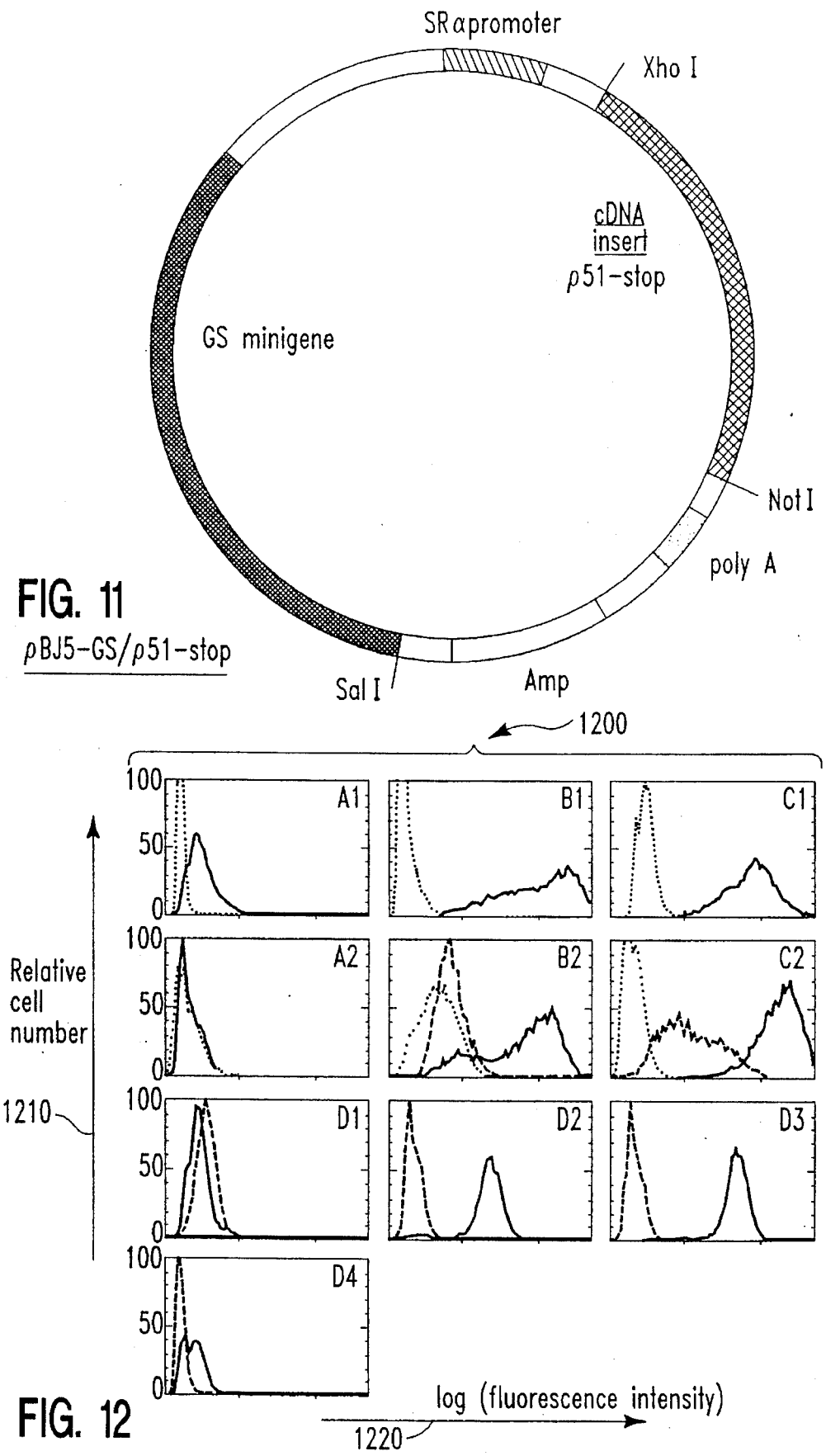
FIG. 11 shows a schematic diagram of the expression vector pBJ5-GS/p51-stop.
FIG. 12 shows graphs 1200 of flow cytometric analyses of CHO cells transfected with lipid-linked forms of FcRn. A1,B1, and C1 show staining of cells by anti-p51 (secondary antibody is a phycoerythrin-conjugated F(ab')$_2$ fragment of anti-rabbit IgG). A2,B2, and C2 show staining by 2B10C11 (anti-rat $\beta_2$m; secondary antibody is fluorescein-labeled goat anti-mouse IgG). ....., represents staining with secondary antibody alone; _____, represents staining with primary and secondary antibodies;_ _ _ _, represents staining with primary and secondary antibodies, cells subsequently treated with phospholipase C and reanalyzed. The vertical axis 1210 units are relative cell number, and the horizontal axis 1220 units are log(fluorescence intensity) for all graphs. (Because the anti-p51 serum is cytotoxic for the transfected cells, the difference in staining after phospholipase C treatment is difficult to detect and is shown only for staining by 2B10C11.) Cells were untransfected, A1 and A2; or were transfected with p51-DAF/$\beta_2$m, B1 and B2; or were transfected with p51-stop/$\beta_2$m-DAF, C1 and C2. D1–D4 shows binding of fluorescein-labeled rat Fc to transfected cell lines at pH 8 (- - -), versus pH 6.5 (—). Cells were untransfected, D1; or were transfected with p-51 DAF/$\beta_2$m, D2; p51-stop/$\beta_2$m-DAF, D3; or p51-DAF, D4.

Both lipid-linked forms of FcRn were determined to bind labeled rat Fc at pH 6.5, but not at pH 8.0, as shown in FIG. 12 at D1–D4. This reproduces the physiological pH dependence of Fc binding, confirming that the presence of the PI anchor on one of the two chains of the modified FcRn heterodimer does not interfere with proper heterodimer formation or Fc binding. Diminished binding of rat Fc to lipid-linked heavy chains transfected in the absence of rat $\beta_2$m, as shown in FIG. 12 at D4, suggests that the FcRn molecule is not fully functional in the absence of rat $\beta_2$m, even when a hamster or bovine $\beta_2$m light chain is provided for potential association. Thus, in the most preferred embodiment of the present invention, the $\beta_2$m associated with the sFcRn heavy chain is the corresponding wild type $\beta_2$m.

Because the truncated p51 (FcRn heavy chain) was capable of being transported to the surface of the cell, and because little or no exchange of rat $\beta_2$m with bovine or hamster $\beta_2$m present in the process medium occurred, applicants next attempted to make a secreted, soluble form of FcRn.

As previously disclosed, the starting material described herein for the method of producing the more preferred pHsFcR embodiment, secreted pHsFcR, was the cDNA for FcRn (the membrane-bound Fc receptor on the intestinal epithelial cells of newborn rats). It is understood that the present method for producing pHsFcRn can be applied to other membrane-bound vertebrate Fc receptors as well.

The FcRn, found in nature attached to cell membranes is limited in its functional uses. The pHsFcRn of the present invention, freed from the cell membrane, is available for attachment to any compatible, functional surface.

METHOD FOR PRODUCING SOLUBLE Fc RECEPTOR

Reagents

Rat IgG, fluorescein-conjugated rat Fc, and phycoerythrin-conjugated F(ab')$_2$ fragments of goat anti-rabbit IgG were from Jackson ImmunoResearch. Fluorescein-conjugated goat anti-mouse was from Cappel Products. Goat anti-rabbit IgG-peroxidase conjugate and purified rabbit anti-human $\beta_2$m IgG for Western blots were from Boehringer Mannheim. CNBr-activated Sepharose 4B was from Pharmacia. Endoglycosidase F/N-glycosidase F was from Boehringer Mannheim. Methionine sulfoximine (MSX), phospholipase C, and lentil lectin-Sepharose 4B were from Sigma. Dulbecco's modified Eagle's medium (DMEM), e minimum essential medium (eMEM), and dialyzed fetal bovine serum were from Irvine Scientific and GIBCO/BRL. Anti-p51, a rabbit polyclonal antiserum against the FcRn heavy chain was supplied by Neil E. Simister of Brandeis University, Waltham, Mass. 2B10C11, a mouse monoclonal antibody against rat $\beta_2$m, was supplied by Lennart Logdgerg of Sandoz Pharmacological Corporation. The pBJ1 and pBJ5 plasmid vectors were obtained from the Mark Davis Laboratory at Stanford University.

It should be mentioned here that the pHsFcR of the present invention, if conjugated with a reporter group such as phycoerythrin, fluorescein or peroxidase, can be used in place of some of the reagents listed above; eg. in place of fluorescein-conjugated goat anti-mouse and goat anti-rabbit IgG-peroxidase conjugate.

EXAMPLE 1

Method of Producing a Vector for Expression of the cDNA for a Lipid-Linked Truncated FcRn Heavy Chain and a Wild-Type $\beta_2$m Molecular biological experiments were performed by standard methods, as described by J. Sambrook, et al. in "Molecular Cloning: A Laboratory Manual" (Cold Spring Harbor Lab, Cold Spring Harbor N.Y.) 2nd Ed. (1989). The p51-DAF chimera was constructed by methods similar to those used for the expression of a lipid-linked form of the T-cell antigen receptor, as described by A. Y. Lin et al. in *Science*, Vol. 249, pp. 677–679 (1990). The chimeric protein consisted of the phosphatidyl inositol (PI)-anchoring signal of decay-accelerating factor (DAF; residues 311–347; as described by I. W. Caras et al. in *Science*, Vol. 238, pp. 1280–1283 (1987)) fused C-terminal to amino acid 269 of the FcRn heavy chain. The sequence for this PI-anchoring signal (as given in FIG. 2A) is as follows:

| Pro | Asn | Lys | Gly | Ser | Gly | Thr | Thr | Ser | Gly | Thr | Thr | Arg | Leu | Leu | Ser | Gly | His |
|-----|-----|-----|-----|-----|-----|-----|-----|-----|-----|-----|-----|-----|-----|-----|-----|-----|-----|
| Thr | Cys | Phe | Thr | Leu | Thr | Gly | Leu | Leu | Gly | Thr | Leu | Val | Thr | Met | Gly | Leu | Leu |
| Thr.|     |     |     |     |     |     |     |     |     |     |     |     |     |     |     |     |     | pBS/p51-DAF, not shown in the FIGS., was constructed as follows:

(a) The cDNA encoding the DAF PI-anchoring signal, residues 311–347, as described by I. W. Caras et al., referenced above, was inserted into the polylinker of pBluescript SK(−) at the plasmid's unique EcoR V restriction site, using techniques known in the art, to generate the plasmid pBS/DAF. Bluescript SK(−) is available from Stratagene.

(b) A Bam HI fragment comprising the full length FcRn heavy chain cDNA was obtained from N. E. Simister of Brandeis University. This cDNA can be produced using techniques known in the art.

(c) pBS/DAF was cleaved using the restriction enzyme Bam HI to generate a linearized pBS/DAF.

(d) The Bam HI DNA fragment from step (b) was ligated to the linearized pBS/DAF of step (c) to produce pBS/DAF/p51.

(e) Oligonucleotide-directed in vitro deletional mutagenesis (of the kind described by T. A. Kunkel et al., in Methods Enzymol, Vol. 154, pp. 367–382 (1987)) was used on pBS/DAF/p51 of step (d) to fuse the DNA sequence encoding the PI anchoring signal of DAF to the 3'end of the DNA codon encoding amino acid 269 of the FcRn heavychain, producing the plasmid pBS/p51-DAF.

Figure 6:
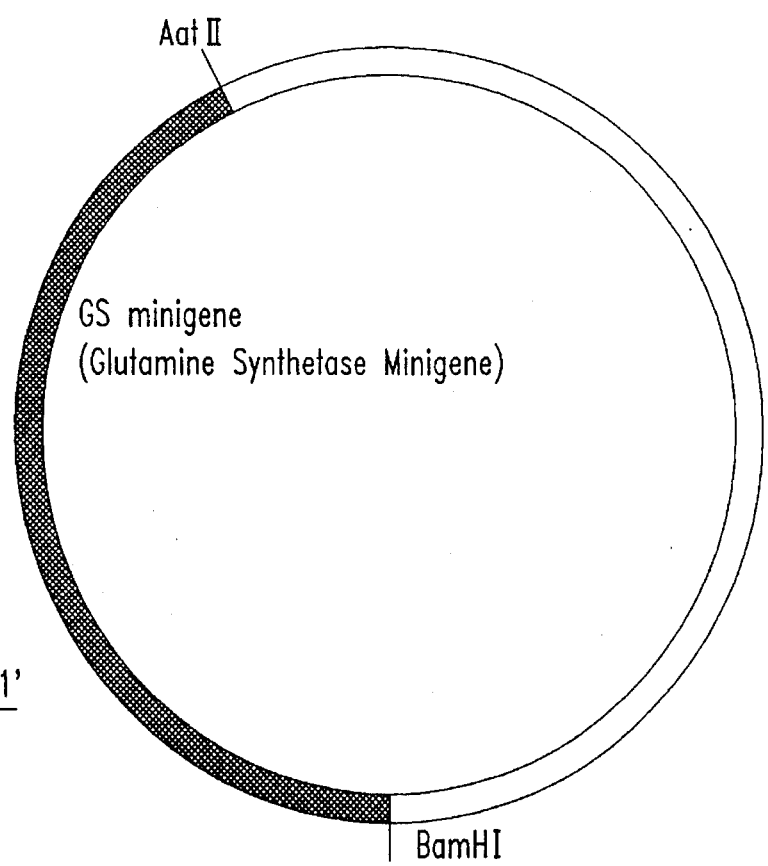
FIG. 6 shows a schematic diagram of a plasmid pSV-LGS.1, which is a source of the glutamine synthetase selectable marker.

The pBJ5-GS expression vector (schematic shown in FIG. 3) is a derivative of pBJ-5, (schematic shown in FIG. 4). pBJ-5 was derived from pBJ-1 (schematic shown in FIG. 5) by the elimination of the SAL I restriction site located between the ampicillin restriction gene and the poly A addition signal, using techniques known in the art. pBJ-1 was derived from pcDL-SRα296 (not shown in the FIGS.) in the same manner that pBJ1-Neo was derived (described by A. Y. Lin et al., Science, Vol. 249, pp. 677–679 (1990)), with the single exception that a neomycin gene was not inserted during construction of the PBJ1 plasmid. The pBJ-1 and pBJ-5 plasmid vectors were obtained from the Mark Davis laboratory at Stanford University.

pBJ5-GS, shown in FIG. 3, was constructed as follows:

(a) The CellTech vector pSVLGS.1, (schematic shown in FIG. 6) was cleaved using the restriction enzymes Aat II and BAM HI to generate a DNA fragment comprising the GS minigene. pSVLGS.1 is available from Celltech Limited, Berkshire, U.K.

(b) The single-stranded DNA tails on the ends of the GS minigene fragment described above were treated using 4-dNTP (dATP, dGTP, dTTP and dCTP combined) and $T_4$ DNA ligase to form blunt ends, using techniques known in the art.

(c) pBluescript SK(−) was cleaved with Xho I and this linearized plasmid was treated with 4-dNTP and $T_4$ ligase to form blunt ends, using techniques known in the art.

(d) The blunt-ended GS minigene fragment from step (b) was ligated to the blunt-ended pBluescript SK(−) from step (c) to produce a circular plasmid pBS/GS (not shown in the FIGS.), using techniques known in the art.

(e) The pBS/GS plasmid from step (d) was cleaved using the restriction enzymes Sal I and Xho I to generate a DNA fragment comprising the GS minigene, using techniques known in the art.

(f) The pBJ5 vector described above (schematic shown in FIG.4) was linearized by cutting it with the Sal I restriction enzyme.

Figure 3:
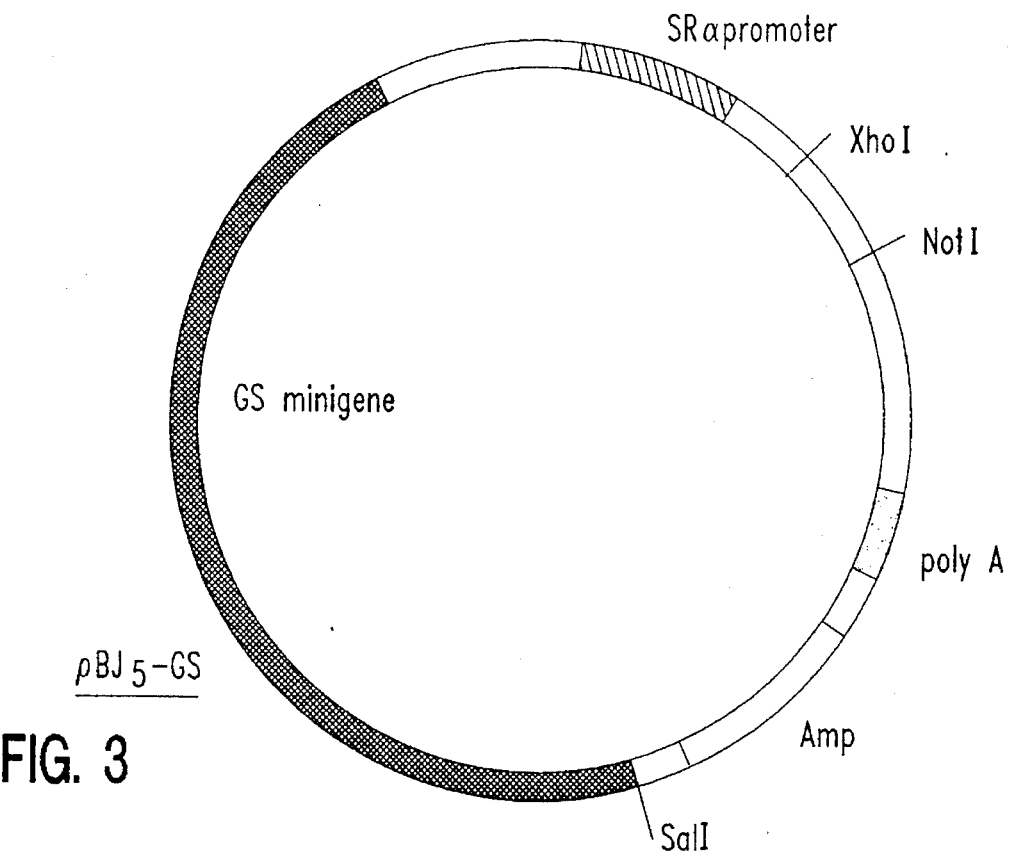
FIG. 3 shows a schematic diagram of the expression vector pBJ5-GS.
Figure 4:
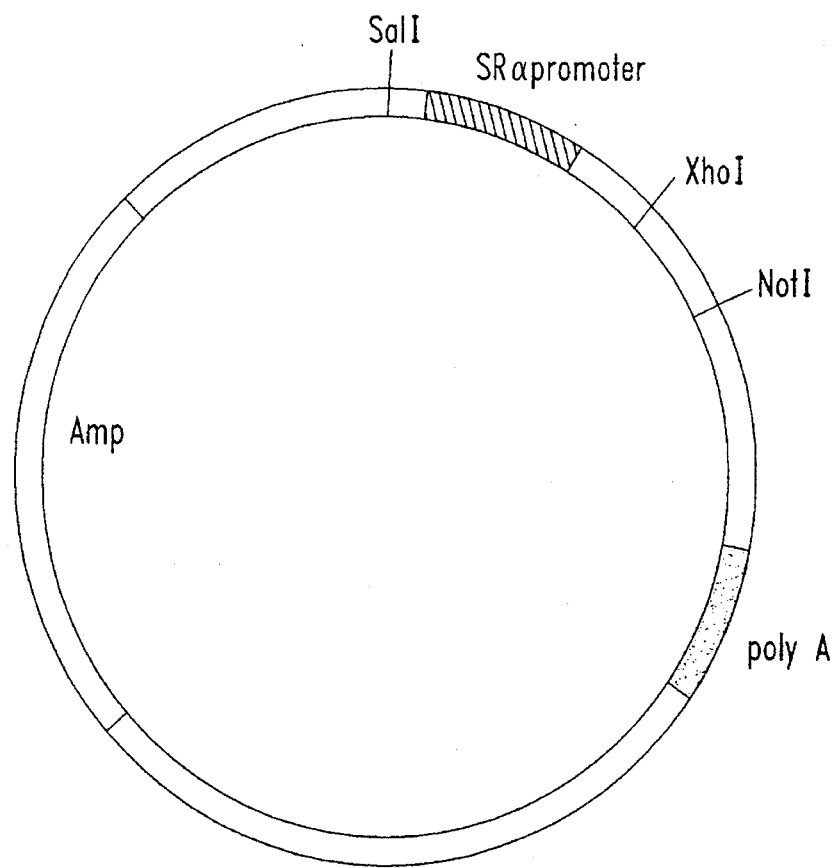
FIG. 4 shows a schematic diagram of the expression vector pBJ5.

(g) The GS minigene fragment from step (e) was ligated to the linearized pBJ5 vector from step (f) to produce the circular expression vector pBJ5-GS shown in FIG. 3. pBJ5-GS employs the glutamine synthetase gene as a selectable marker and means of gene amplification in the presence of the drug MSX, a system developed by C. R. Bebbington et al. of Celltech and described in DNA Cloning, ed. D. M. Glover IRL, Oxford, Vol. 3 chapter 8, p. 163 (1987).

pBJ5-GS/p51-DAF (schematic shown in FIG. 7) was constructed as follows:

(a) The p51-DAF cDNA was cleaved from the pBS/p51-DAF described above using Xho I and Not I restriction enzymes, using techniques known in the art.

(b) The circular pBJ5-GS, expression vector shown in FIG. 3, was linearized using Xho I and Not I restriction enzymes, using techniques known in the art.

Figure 7:
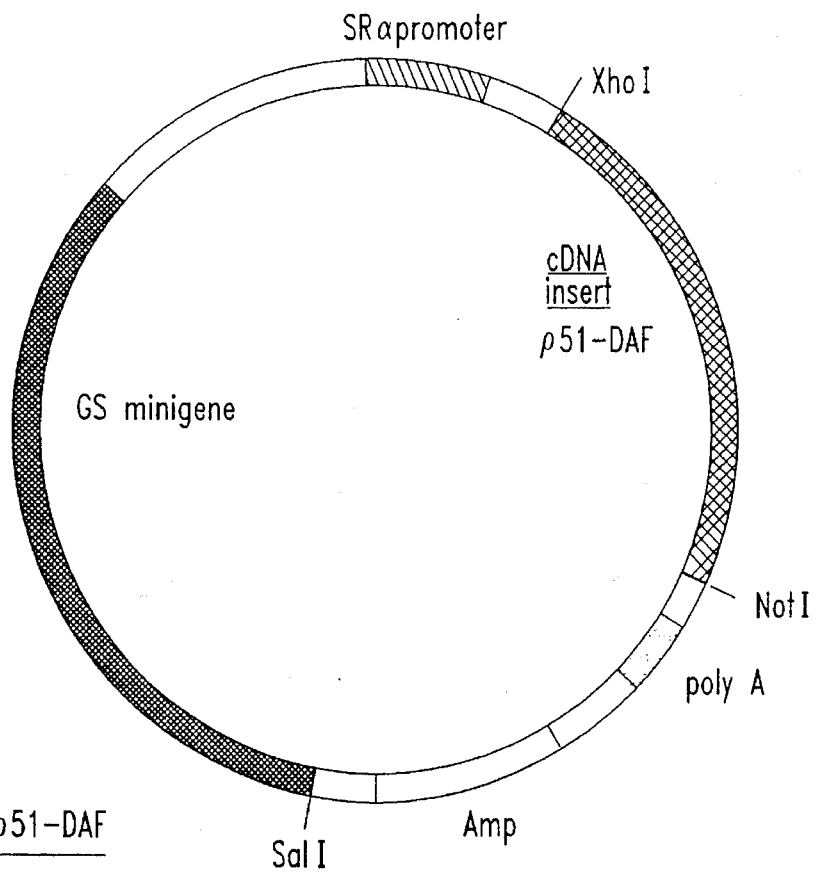
FIG. 7 shows a schematic diagram of the expression vector pBJ5-GS/p51-DAF.

(c) The p51-DAF cDNA of step (a) was then ligated into the linearized pBJ5-GS from step (b), using techniques known in the art, to produce the expression vector pBJ5-GS/p51-DAF shown in FIG. 7.

PBJ1/$\beta_2$m (schematic shown in FIG. 8) was constructed as follows:

(a) A Bam HI fragment containing the full length rat $\beta_2$m cDNA was obtained from N. E. Simister of Brandeis University. This cDNA can be produced using techniques known in the art.

(b) pBluescript SK(−) was cleaved using BAM HI, using techniques known in the art.

(c) The BAMHI fragment described in (a) was ligated to the linearized pBluescript SK(−) of step (b) to produce pBSβ$_2$m (not shown in the FIGS), using techniques known in the art.

(d) pBS/β$_2$m was cleaved using the restriction enzymes Not I and Xho I to generate a DNA fragment comprising the full length rat β$_2$m cDNA, using techniques known in the art.

(e) pBJ1 (schematic shown in FIG. 5) was cleaved using restriction enzymes Xho I and Not I, using techniques known in the art.

Figure 8:
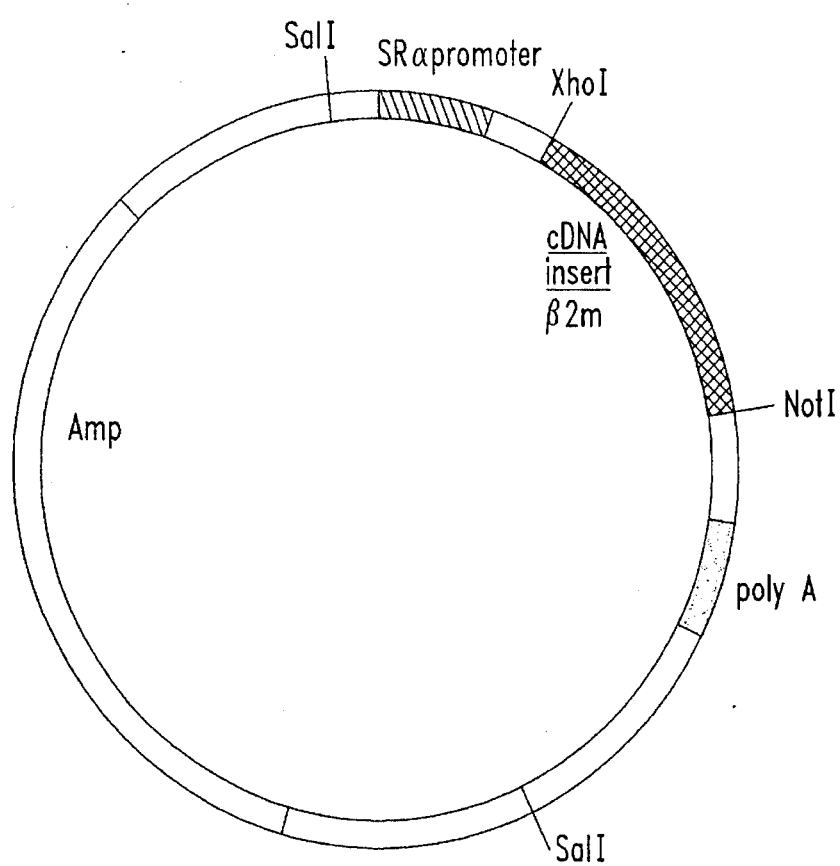
FIG. 8 shows a schematic diagram of the Expression vector pBJ1/$\beta_2$m.

(f) The DNA fragment from step (d) was ligated to the linearized pBJ1 of step (e) to produce pBJ1/β$_2$m, shown in FIG. 8, using techniques known in the art.

The expression vector pBJ5-GS/p51-DAF/β$_2$m (schematic shown in FIG. 2B, wherein cDNAs p51-DAF and β$_2$m are inserted) was constructed as follows:

(a) The pBJ5-GS/p51-DAF, shown in FIG. 7, was cleaved using the restriction enzyme Sal I, using techniques known in the art.

(b) The pBJ1/β$_2$m, shown in FIG. 8, was cleaved using the restriction enzyme Sal I to generate a DNA fragment comprising the full length rat β$_2$m cDNA, the SRe promoter, and the poly A addition signal, using techniques known in the art.

(c) The DNA fragment from step (b) was ligated to the linearized pBJ5-GS/p51-DAF from step (a) to produce circular expression vector pBJ5-GS/p51-DAF/β$_2$m, using techniques known in the art.

EXAMPLE 2

Method of Producing a Vector for Expression of the eDNA for a Lipid-Linked β$_2$m and a Truncated FcRn Heavy Chain Molecular biological experiments were performed by standard methods, as described by J. Sambrook, et al. in "Molecular Cloning: A Laboratory Manual" (Cold Spring Harbor Lab, Cold Spring Harbor N.Y.) 2nd Ed. (1989). The β$_2$m-DAF chimera was constructed by methods similar to those used for the expression of a lipid-linked form of the T-cell antigen receptor, as described by A. Y. Lin et al. in Science, Vol. 249, pp. 677–679 (1990). The chimeric protein consisted of the phosphatidyl inositol (PI)-anchoring signal of decay-accelerating factor (DAF; residues 311–347; as described by I. W. Caras et al. in Science, Vol. 238, pp.

1280–1283 (1987)) fused C-terminal to the final amino acid 99 of $\beta_2$m.

pBS/$\beta_2$m-DAF, not shown in the FIGS., was constructed as follows:

(a) A Bam HI fragment comprising the full length $\beta_2$m light chain cDNA was obtained from N. E. Simister of Brandeis University. This cDNA can be produced using techniques known in the art.

(b) pBS/DAF produced as described in EXAMPLE 1, was cleaved using the restriction enzyme Bam HI to generate a linearized pBS/DAF.

(c) The Bam HI DNA fragment from step (a) was ligated to the linearized pBS/DAF of step (b) to produce pBS/DAF/$\beta_2$m.

(d) Oligonucleotide-directed in vitro deletional mutagenesis (of the kind described by T. A. Kunkel et al., in Methods Enzymol, Vol. 154, pp. 367–382 (1987)) was used on pBS/DAF/$\beta_2$m of step (d) to fuse the DNA sequence encoding the PI anchoring signal of DAF to the 3'end of the DNA codon encoding amino acid 269 of the $\beta_2$m light chain, producing the plasmid pBS/$\beta_2$m-DAF.

pBJ5-GS/$\beta_2$m-DAF (schematic shown in FIG. 9), was constructed as follows:

(a) The $\beta_2$m-DAF cDNA was cleaved from pBs/$\beta_2$m-DAF using Xho I and Not I restriction enzymes, using techniques known in the art.

(b) The circular pBJ5-GS expression vector, shown in FIG. 3, was linearized using Xho I and Not I restriction enzymes, using techniques known in the art.

Figure 9:
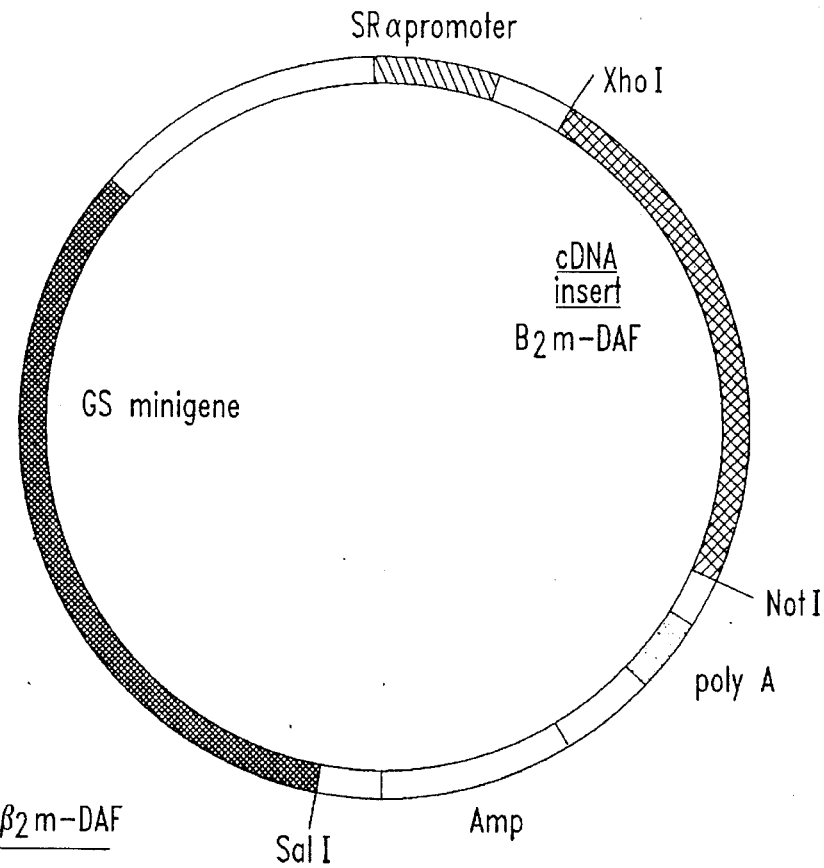
FIG. 9 shows a schematic diagram of the expression vector pBJ5-GS/$\beta_2$m-DAF.

(c) The $\beta_2$m-DAF cDNA of step (a) was then ligated into the linearized pBJ5-GS of step (b), using techniques known in the art, to produce the pBJ5-GS/$\beta_2$m-DAF shown in FIG. 9.

pBS/p51-stop (not shown in FIGS.) was constructed as follows: .

(a) A Bam HI fragment comprising the full length FcRn heavy chain cDNA was obtained as previously described.

(b) pBluescript SK(–) was cleaved using the restriction enzyme Bam HI to generate a linearized pBluescript SK(–).

(c) The Bam HI DNA fragment of step (a) was ligated to the linearized pBluescript SK(–) of step (b), using techniques known in the art, to produce pBS/p51 (not shown in the FIGS.).

(d) Oligonucleotide-directed in vitro deletional mutagenesis (of the kind described by T. A. Kunkel et al.) was used on pBS/p51 of step (c) to insert a translational stop codon immediately 3' of the codon encoding amino acid 269 of the FcRn heavy chain, producing the plasmid pBS/p51-stop (comprising the modified FcRn heavy chain cDNA, p51-stop).

pBJ1/p51-stop, shown in FIG. 10, was constructed as follows:

(a) The pBS/p51-stop described above was cleaved using the restriction enzymes Not I and Xho I to generate a DNA fragment comprising the p51-stop cDNA, using techniques known in the art.

Figure 5:
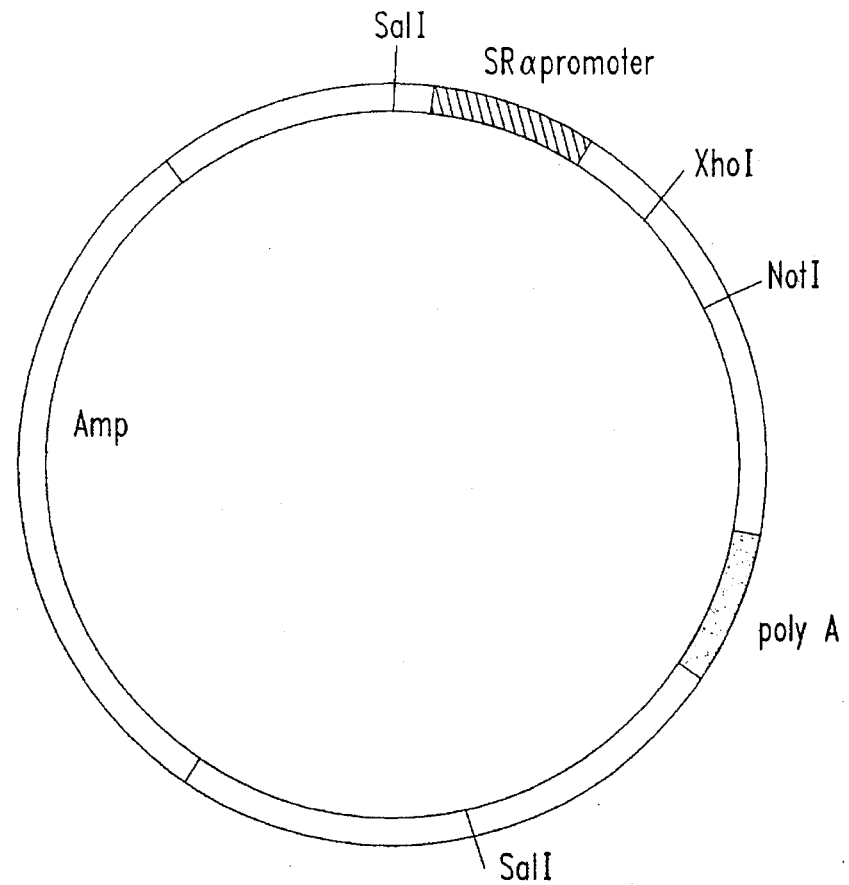
FIG. 5 shows a schematic diagram of the expression vector pBJ1.

(b) pBJ1, shown in FIG. 5, was cleaved using restriction enzymes Xho I and Not I using techniques known in the art.

Figure 10:
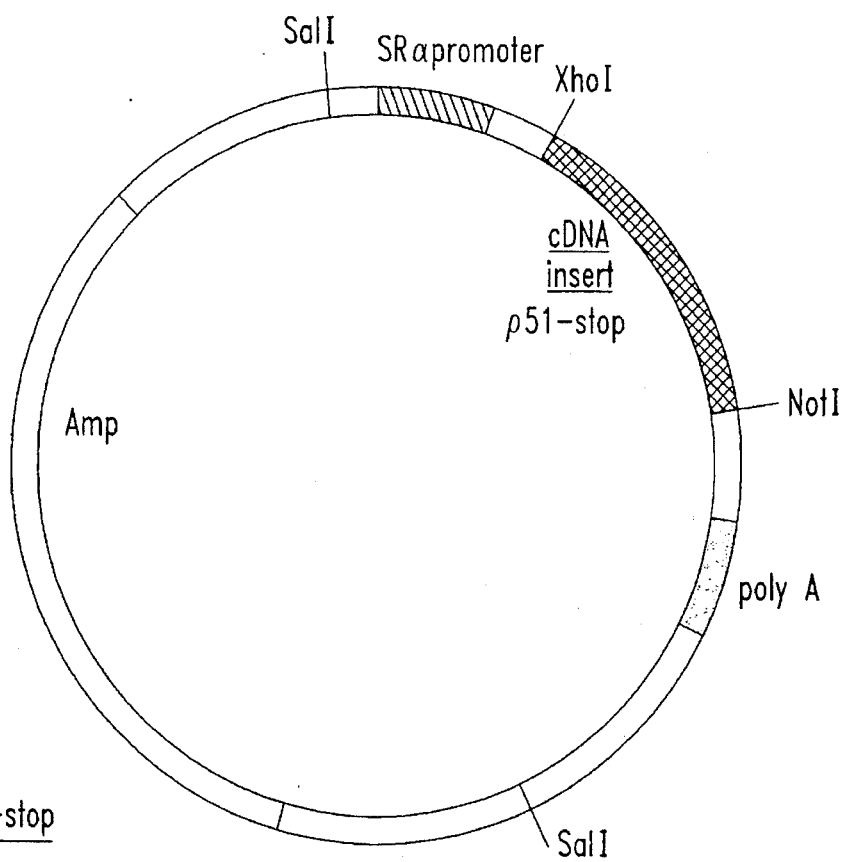
FIG. 10 shows a schematic diagram of the expression vector pBJ1/p51-stop.

(c) The DNA fragment from step (a) was ligated to the linearized pBJ1 of step (b) to produce pBJ1/p51-stop, shown in FIG. 10, using techniques known in the art.

The expression vector .pBJ5-GS/p51-stop/$\beta_2$m-DAF (shown in FIG. 2B, wherein cDNAs $\beta_2$m-DAF and p51-stop are inserted) was constructed as follows:

(a) The pBJ5-GS/$\beta_2$m-DAF, shown in FIG. 9, was cleaved using the restriction enzyme Sal I, using techniques known in the art.

(b) The pBJ1/p51-stop, shown in FIG. 10, was cleaved using the restriction enzyme Sal I to generate a DNA fragment comprising the p51-stop cDNA, the SRa promoter, and the poly A addition signal, using techniques known in the art.

(c) The DNA fragment from step (b) was ligated to the linearized pBJ5-GS/$\beta_2$m-DAF from step (a), using techniques known in the art, to produce circular expression vector pBJ5-GS/p51-stop/$\beta_2$m-DAF.

EXAMPLE 3

Method of Producing a Vector for Expression of the cDNA for a Truncated FcRn Heavy Chain and a Wild-Type $\beta_2$m Molecular biological experiments were performed by standard methods, as described by J. Sambrook, et al. in "Molecular Cloning: A Laboratory Manual" (Cold Spring Harbor Lab, Cold Spring Harbor N.Y.) 2nd Ed. (1989).

pBJ5-GS/p51-stop (schematic shown in FIG. 11), was constructed as follows:

(a) pBS/p51-stop prepared as described in Example 2 above, was cleaved using the restriction enzymes Xho I and Not X to generate a DNA fragment comprising the p51-stop cDNA, using techniques known in the art.

(b) The pBJ5-GS prepared as described in Example 1 above and shown in FIG. 3, was linearized using Xho I and Not I restriction enzymes, using techniques known in the art.

(c) The DNA fragment from step (a) was ligated to the linearized pBJ5-GS from step (b) to produce pBJ5-GS/p51-stop as shown in FIG. 11, using techniques known in the art.

pBJ5-GS/p51-stop/$\beta_2$m (schematic shown in FIG. 2B, wherein cDNAs p51-stop and $\beta_2$m are inserted) was constructed as follows:

(a) pBJ1/$\beta_2$m produced as described in Example 1 and shown in FIG. 8 was cleaved using the Sal I restriction enzyme to generate a DNA fragment comprising the full length $\beta_2$m eDNA, the SRe promoter and the poly A addition signal, using techniques known in the art.

(b) pBJ5-GS/p51-stop produced as described above and shown in FIG. 11 was cleaved using the Sal I restriction enzyme, using techniques known in the art.

(c) The DNA fragment from step (a) was ligated to the linearized pBJ5-GS/p51-stop from step (b), using techniques known in the art, to produce the circular expression vector pBJ5-GS/p51-stop/$\beta_2$m.

EXAMPLE 4

Production of the Three FcRn Forms in CHO Cells

Each of the three expression vectors described in Examples 1–3 was individually transfected into CHO (Chinese Hamster Ovary) cells by the following calcium phosphate procedure (Stratagens). The CHO cell line was CHO-K1, obtained from ATCC (American Type Culture Collection), catalog number CCL61. A calcium phosphate/

DNA precipitate containing 30 μg of pure DNA, or no DNA as a mock control, was added to CHO cells in 10 ml of fresh DMEM with serum. Selection and amplification of the glutamine synthetase gene were carried out according to the following protocol. The next day, the cells were washed three times with eMEM without serum and then incubated in a αMEM with 10% dialyzed fetal bovine serum and 25 μM MSX. Viable CHO cells containing the transfected expression vectors described above were visible after two weeks and were isolated and grown (using standard techniques known in the art for CHO cell growth) in 24 well plates in eMEM with a 10% dialyzed fetal bovine serum and 25 μM MSX. The isolation and growth of viable cells was repeated to produce several distinct homogeneous populations of transfected cells (clones of cells).

Clones transfected with the two lipid-linked forms of FcRn were tested for expression of both protein subunits by immunofluorescence with anti-p51 and 2B10C11. Clones expressing the desired lipid-linked form of FcRn were put in six-well plates and submitted to increasing MSX concentrations from 50 to 500 μM, to select for cells in which the transfected genes had been amplified.

Clones expressing the desired lipid-linked form of FcRn were also tested for their ability to differentially bind rat Fc at pH 6.5 as follows: 106 cells were incubated in suspension for 1 hour at room temperature in 500 μl of phosphate-buffered saline (pH 6.5 or pH 8.0) with fluorescein-conjugated rat Fc (0.5 μM) and then washed twice. The cell pellet was resuspended in 1 ml of buffer at the appropriate pH and analyzed by flow cytometry using an Ortho cell sorter available from Ortho Pharmaceutical Company of Raritan, New Jersey (U.S.A.).

Supernatants from CHO clones transfected by pBJ5-GS/p51-stop/$\beta_2$m (the secretable, soluble form of FcRn) were tested for secreted FcRn heterodimer by Western blotting with anti-p51 and a rabbit anti-human $\beta_2$m antiserum (cross-reactive with rat $\beta_2$m). Clones expressing the secreted, soluble form of FcRn were put in six-well plates and submitted to increasing MSX concentrations from 50 to 500 μM, to select for cells in which the transfected genes had been amplified.

Phospholipase C Treatment of Clones Expressing the Lipid-Linked Form of FcRn

Cleavage of lipid-linked proteins was done as described by A. Y. Lin et al., referenced above, but using a stock of phospholipase C containing PI-PLC (Sigma P6135; 1 mg/ml), which was added to 107 cells at a 100-fold dilution. Cells were incubated for 2 hours at 37° C. in an atmosphere having controlled humidity and carbon dioxide content, within the standard technology ranges. The above cleavage reaction produced a soluble pHsFcRn, derived from each lipid-linked form of FcRn, which soluble pHsFcR could be harvested via the purification technique described below.

Purification of pHsFcRn by Affinity Chromatography and Biochemical Analysis

Rat IgG (70 mg) was covalently linked to 7 ml of CNBr-activated Sepharose (10 mg/ml) according to the manufacturer's directions. The pH of 100–500 ml of either supernatant from a CHO clone secreting sFcRnheterodimer growing in 100 μM MSX or cleavage reaction solution containing pHsFcR was decreased to pH 6.5 and put on the column at a constant flow rate of 20 ml/hr at 4° C., and the column was washed with 300 ml of 50 mM sodium phosphate, pH 6.5/0.05% $NaN_3$. Elution of pHsFcRn was initiated with 50 mM sodium phosphate, pH 8.0/0.05% $NaN_3$. Fractions of 2 ml were collected and their optical density at 280 nm measured. Typically, ≈10 mg of secreted pHsFcRn heterodimer [quantified by bicinchoninic acid (BCA) assay; Pierce] was eluted in six fractions from 250 ml of supernatant harvested from $10^8$–$10^9$ cells. The protein was concentrated by Centricon 10000 concentration devices available from Amicon Corp.

pHsFcR derived from lipid-linked FcRn was also obtained using the above-described purification technique and was evaluated along with the secreted pHsFcR as described below.

EXAMPLE 5

ANALYTICAL DATA CONFIRMING THE PRODUCTION OF SOLUBLE FcRn (pHsFcRn) WAS OBTAINED AS PRESENTED BELOW

N-Terminal Sequencing.

N-terminal sequencing was performed on 20–40 μg of purified secreted pHsFcRn in a phosphate buffer dried on a poly(vinylidene difluoride) membrane (in the manner described by P. Matsudaira, J. Biol. Chem. Vol. 262, pp. 10035–10038 (1987) and inserted into an Applied Biosystems model 4778 sequencer reaction cartridge. CD Spectra.

A Jasko J-600 spectropolarimeter was used in the wavelength range of 190 to 260 nm with a 0.1 mm cell. Purified HLA-B40 (A Class I MHC molecule) (supplied by Don Wiley and Anastasia Haykov, of Harvard University, Cambridge, Mass.,) and secreted pHsFcRn heterodimer were concentrated to 0.1–0.5 mg/ml in 20 mM sodium phosphate (pH 8.0). The percent helix, β-strand, and disordered structure (random) was estimated by fitting the spectra to reference data (from N. Greenfield et al., Biochemistry, Vol. 8, pp. 4108–4115 (1969) with a nonrestrained least-squares algorithm.

Crystallization of Secreted pHsFcRn.

Crystals were grown by vapor diffusion from protein solutions (20 mg/ml) in 10 mM Pipes, pH 6.5/0.05% $NAN_3$, in 2-μl droplets with 24.0% (wt/vol) polyethylene glycol 3350, 2.0% (wt/vol) saturated ammonium sulfate, and 100 mM Pipes (pH 6.5).

SUMMARY OF RESULTS FROM EXAMPLES 1 THROUGH 5

Expression of Two Lipid-Linked (membrane-bound) Forms of FcRn.

An expression vector, as illustrated in FIG. 2B, containing the hamster glutamine synthetase gene 252 (for selection and amplification), the gene encoding the extracellular portion of the FcRn heavy chain fused in-frame to the cDNA from DAF encoding its lipid attachment signal (p51-DAF), and the rat $\beta_2$m gene was transfected into CHO cells. Stable lines were generated and the transfected gene was amplified by selection with MSX. (Cell surface expression of FcRn heavy and light chains were detected by immunostaining with anti-p51 and anti-rat $\beta_2$m antibodies as shown in FIG. 12 at B1 and B2; and the amount of rat $\beta_2$m detected was reduced after treatment with PI-PLC, as illustrated in FIG. 12 at B2 (- - -). CHO cells expressing these lipid-linked FcRn heterodimers bound rat Fc. The physiological pH dependence of Fc binding observed in nature was reproduced, in that binding was observed at pH 6.5 but not at pH 8.0., as illustrated in FIG. 3 at D2 and D3, wherein— represents pH 6.5, and - - - - represents pH 8. Binding of labeled Fc was inhibited by addition of unlabeled rat IgG or rat Fc at 100 µg/ml, but not by the equivalent amount of an unrelated protein. Expression of the lipid-linked FcRn heavy chain in the absence of rat $\beta_2$m was at a level comparable to the expression in the presence of rat $\beta_2$m (data not shown), but the binding of fluorescein-conjugated rat Fc was diminished, as illustrated in FIG. 12 at D4.

The second lipid-linked form of FcRn was expressed by transfecting a plasmid containing the DNA encoding the DAF PI-attachment signal fused to the rat $\beta_2$m gene, together with the gene encoding the FcRn heavy chain truncated with an in-frame stop codon after amino acid 269 (p51-stop), and the glutamine synthetase gene, as illustrated in FIG. 2B. Stable CHO lines expressing this lipidlinked form of FcRn were generated by selection with MSX and stained with the anti-p51 and anti-rat $\beta_2$m antibodies as shown in FIG. 12 at C1 and C2; and the amount of rat $\beta_2$m detected was reduced after treatment with PI-PLC, as illustrated in FIG. 12 at C2 (- - -). The FcRn/$\beta_2$m heterodimers also showed the expected pH dependence of Fc binding, as illustrated in FIG. 3 at D3. Expression levels of the two forms of lipid-linked FcRn heterodimers appeared comparable, as illustrated by comparison of FIG. 3 at B1 and C1.

Expression of Secreted sFcRn

An expression vector (FIG. 2B) containing the glutamine synthetase gene, the truncated FcRn heavy chain gene, and the rat $\beta_2$m gene was transfected into CHO cells. Media collected from individual clones were assayed for secretion of pHsFcRn heterodimers by Western blotting aliquots of supernatants with antibodies specific for the heavy and light chains. Positive clones were amplified with increasing amounts of MSX. Medium (250 ml) from a high-expressing clone growing in 100 µM MSX was adjusted to pH 6.5 and passed over a rat IgG affinity column. The column was extensively washed, and pHsFcRn heterodimers were eluted by changing the pH to 8.0, yielding ≈10 mg of purified protein. The high-expressing CHO clone was grown in a Cell Pharm II hollow-fiber bioreactor device (Unisyn Fibertec) in the presence of 100 µM MSX. The yield of soluble pHsFcRn was typically 7–10 mg per daily harvest.

Figure 13:
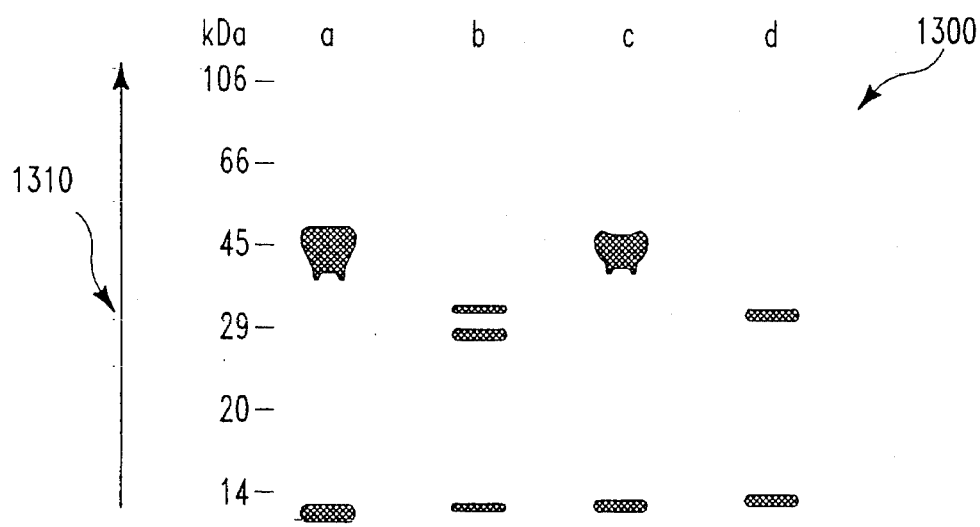
FIG. 13 shows an SDS/17.5% PAGE comparison of purified secreted FcRn before (lanes a and c) and after (lanes b and d) treatment with endoglycosidase F/N-glycosidase F. Samples were run under nonreducing (lanes a and b) or reducing (lanes c and d) conditions. The vertical axis 1310 units are kDa (kilo Daltons).

Purified secreted pHsFcRn was analyzed by SDS/17.5% PAGE, as illustrated in FIG. 13. FIG. 13 shows SDS/17.5% PAGE comparison of purified secreted pHFcRn before (lanes a and c) and after (lanes b and d) treatment with endoglycosidase F/N-glycosidase F. Samples were run under nonreducing (lanes a and b) or reducing (lanes c and d) conditions. Under either reducing or nonreducing conditions, two bands were detected: a sharp band of apparent molecular mass 13 kDa, corresponding to $\beta_2$m, and a broad diffuse band at ≈43 kDa, corresponding to the truncated FcRn heavy chain. Treatment of purified pHsFcRn with a mixture of endoglycosidase F and Nglycosidase F had no effect on the apparent molecular mass of $\beta_2$m, but the majority of the heavy chain shifted its position of migration to 30 kDa, in close agreement with the predicted molecular mass of the unmodified truncated heavy chain (30,274 Daltons). These data suggest that ≈13 kDa of the extra molecular mass of the truncated FcRn heavy chain was due to N-linked glycosides, a figure that is not inconsistent with the utilization of all four potential N-linked glycosylation sites in the FcRn heavy chain sequence. Deglycosylated pHsFcRn retained its ability to bind to the Fc affinity column (data not shown), suggesting that the pHsFcRn carbohydrate moieties were not involved in the interaction between the Fc Receptor and Fc. This functionality in the absence of the heavy chain carbohydrates suggests that it could be possible to produce most of (if not all of) normal functional pHFcR in procaryotic and eukaryotic cell lines that fail to add carbohydrate to newly synthesized proteins.

Purified pHsFcRn was subjected to N-terminal sequence analysis to verify the origin of the $\beta_2$m species associated with the pHsFcRn heavy chain, and to look for possible peptides associated with the FcRn heavy chain. The first 16 residues of bovine $\beta_2$m (as described by M. L. Groves et al., J. Biol. Chem., Vol. 257, pp. 2619–2626 (1982) and rat $\beta_2$m (as described by J. Sundelin et al., Scand. J. Immunol., Vol. 27, pp. 195–199 (1988) differ at amino acid residues 3, 4 and 6 (of the mature protein), and the sequences of hamster (as determined by applicants) and rat $\beta_2$m differ at residues 3, 4, 7 and 11. Two N-terminal sequences in equimolar amounts were identified in the soluble pHsFcRn sample: the sequence AEPRLPLMYHLAAVSD(SEQ. I.D. NO. 1), corresponding to the first 16 amino acids of the mature FcRn heavy chain as described by N. E. Simister et al., Cold Springs Harbor Symp. Quant. Biol. referenced above, and the sequence IQKTPQIQVYSRHPPE(SEQ. I.D. NO. 2), corresponding to the sequence of the first 16 residues of mature rat $\beta_2$m (J. Sundelin et al. as referenced above). No evidence of sequences corresponding to bound peptides was seen.

CD Spectral Comparison of pHsFcRn and MHC Class I Proteins.

Figure 14:
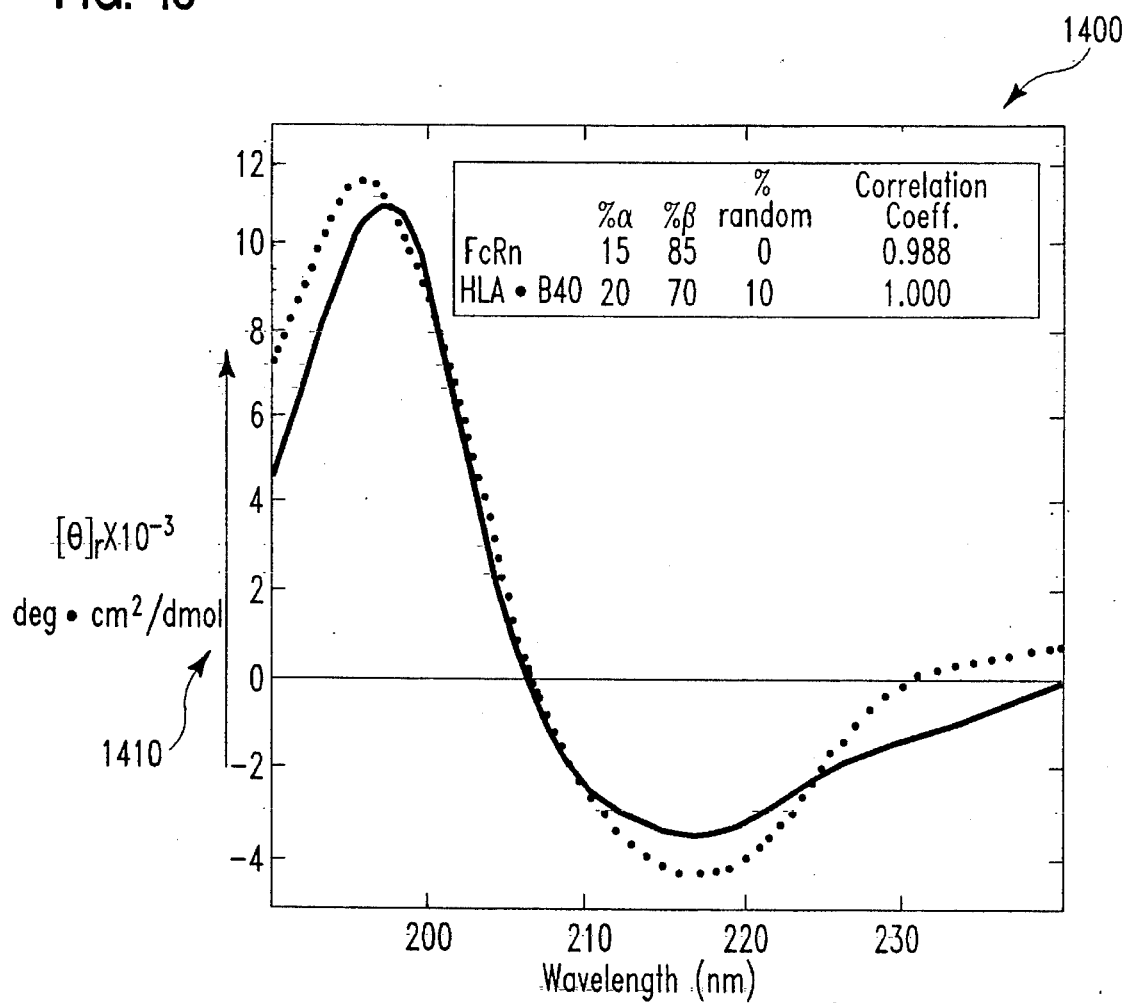
FIG. 14 shows far-UV spectra 500 of FcRn and HLA-B40 (A Class I MHC molecule) expressed as ellipticity per mean residue. _____, represents FcRn (0.24 mg/ml) , and .... represents HLA-B40 (0.12 mg/ml). The vertical axis 1410 units are [$\Theta$]$_{rx}$10$^{-3}$ deg·cm$^2$/dmol. The horizontal axis 1420 units are nm (nanometers).

Analysis of CD spectra of HLA-B40 (a human Class I MHC molecule) and soluble pHsFcRn ( as illustrated in FIG. 14) by a nonrestrained least squares fitting procedure indicated a dominant $\beta$-strand component with a minor helical contribution, similar to that reported previously for HLA-B7 and HLA-A2, although lower amounts of $\beta$-structure were predicted for other class I MHC molecules from CD spectral analyses. The percent helix estimated from our analysis of the spectrum of HLA-B40 agrees well with the amount helix found in Class I MHC crystal structures (≈20% helix); however, our CD spectral data predicts higher $\beta$ structure content (≅60% compared with previous estimates of ≅42%).

FIG. 14 shows Far-UV CD spectra of secreted pHsFcRn and HLA-B40 expressed as ellipticity per mean residue. Comparison of the data shows % α pHsFcRn=15, with % α HLA-B40=20; % $\beta$ of pHsFcRn=85, with % $\beta$HLA-B40= 70; and % random of pHsFcRn=0, with % random of HLA-B40=10. The correlation coefficient for secreted pHsFcRn=0.988 and the correlation coefficient for HLAB-40= 1.0. It is important to mention that the CD spectral information presented herein is consistent within itself but may not be consistent with information generated by others skilled in the art due to subjectivity in the methods of analyzing data.

Crystals of Secreted pHsFcRn.

Soluble, secreted pHsFcRn protein formed crystals of approximate dimensions 0.3 mm×0.1 mm×0.1 mm in space group $C222_1$. The unit cell dimensions were a=126.4 Å, b=191.7 Å, and c=149.6 Å. The asymmetric unit of the crystal was estimated to contain two to four molecules based on average volume to mass ratios ($V_m$) of protein crystals (as described by B. W. Mathews, J. Mol. Biol. Vol. 33, pp. 491–497 (1968)), representing solvent contents between 73% (if two molecules per asymmetric unit) to 32% (if four molecules per asymmetric unit). The crystals diffracted to 3.5 Åresolution using nickel-filtered CuKα radiation from a rotating-anode x-ray generator. Single crystals of a complex of a complex between pHsFcRn and rat Fc have also been obtained by A. H. Huber and the applicants.

Additional General Information

As previously discussed, pertaining to production of secreted pHsFcRn, The gene encoding the truncated FcRn heavy chain was transfected together with the rat $\beta_2$m gene, using the Celltech glutamine synthetase-based amplifiable expression system. With this expression system, a high level of expression can be obtained after an initial selection, and gene amplification is rapidly achieved. Clones secreting soluble FcRn heterodimer were evaluated for relative expression levels by analysis of supernatant samples on Western blots, and a high-expressing clone secreting FcRn at 40 mg/liter was selected at 100 μM MSX. FcRn was purified on a rat IgG affinity column by passing supernatants over the column at pH 6.5 and eluting protein at pH 8.0. This purification scheme is gentle, taking advantage of the physiological pH dependence of Fc binding, thereby avoiding the harsh elution conditions typically necessary for elution from immunoaffinity columns.

SDS/PAGE analysis of purified, secreted pHsFcRn showed two bands corresponding to truncated heavy chain and $\beta_2$m. No evidence of covalent dimerization of the pHsFcRn heavy chain mediated by a disulfide bond was seen by comparison of the mobility under reducing and nonreducing conditions, and purified pHsFcRn was eluted from a gel filtration column at the position expected for a complex of a single heavy and light chain. Microsequencing of pHsFcRn heterodimer revealed the expected N-terminal residues of the heavy chain and rat $\beta_2$m in equimolar amounts, suggesting that $\beta_2$m exchange with bovine $\beta_2$m in the medium or hamster $\beta_2$m inside the CHO cells was either minimal or did not occur.

Because the structurally related Class I MHC molecules are transported to the cell surface with peptides derived from intracellular proteins and appear to depend upon the presence of bound peptide for structural stability, it was of interest whether secreted pHsFcRn heterodimers showed evidence of bound peptide. No other sequences were detectable, suggesting that the pHsFcRn heterodimer was not complexed with a unique peptide. A mixture of peptides would probably not have been detected and cannot be ruled out as a possibility.

Samples of secreted pHsFcRn and the human Class I MHC molecule HLA-B40 were analyzed by CD spectroscopy (FIG. 14). Analysis of CD spectra of the Class I molecule was reasonably consistent with the known Class I x-ray structures and with previously reported CD spectra, as described by D. Lancet et al. in Proc. Natl. Acad. Sci. U.S.A., Vol.76, pp.3844–3848, (1979), and by J. C. Gorga, et al., Proc. Natl. Acad. Sci. U.S.A., Vol. 86, pp. 2321–2325 (1989), suggesting that the molecule is primarily composed of β-structure with a minor α-helical contribution. The CD spectrum of secreted pHsFcRn appears similar, which together with the primary sequence similarity further suggests that the two types of molecules may adopt similar tertiary structures.

The above-described preferred embodiments of the present invention are not intended to limit the scope of the present invention as demonstrated by the claims which follow, as one skilled in the art can, with minimal experimentation, extend the principles of the invention to the claimed scope of the invention.

---

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
        ( A ) LENGTH: 16 amino acid residues
        ( B ) TYPE: Amino acid
        ( C ) STRANDEDNESS:
        ( D ) TOPOLOGY: Linear ( i i ) MOLECULE TYPE: Protein/Peptide ( i i i ) HYPOTHETICAL: No ( i v ) ANTI-SENSE:

( v ) FRAGMENT TYPE: N-terminal ( v i ) ORIGINAL SOURCE:
        ( A ) ORGANISM: Rattus norvegious
        ( B ) STRAIN: Wistar
        ( C ) INDIVIDUAL ISOLATE:
        ( D ) DEVELOPMENTAL STAGE: 11 day- old/germ-line
        ( E ) HAPLOTYPE:
        ( F ) TISSUE TYPE: Proximal third of small intestine
        ( G ) CELL TYPE: Epithelial cells
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:

(B) MAP POSITION:
(C) UNITS:

(ix) FEATURE:
(A) NAME/KEY: This sequence contains the first 16 amino acids of the mature FcRn heavy chain.
(B) LOCATION: FcRn heavy chain (a.a. 1 to 16) from 1 to 16.
(C) IDENTIFICATION METHOD: Purified, soluble FcRn was subjected to N-terminal sequence analysis.
(D) OTHER INFORMATION: This sequence was determined to verify that the secreted, soluble FcRn heavy chain had the same amino terminus as the wild-type transmembrane FcRn heavy chain.

(x) PUBLICATION INFORMATION:
(A) AUTHORS: Simister, N.E.
Mostov, K.E.
(B) TITLE: An Fc receptor structurally related to MHC class I antigens.
(C) JOURNAL: Nature
(D) VOLUME: 337
(E) ISSUE:
(F) PAGES: 184-187
(G) DATE: 12-Jan-1989
(H) DOCUMENT NUMBER:
(I) FILING DATE:
(J) PUBLICATION DATE:
(K) RELEVANT RESIDUES IN SEQ ID NO:1: FROM 1 TO 16.

(x) PUBLICATION INFORMATION:
(A) AUTHORS: Simister, N.E.
Mostov, K.E.
(B) TITLE: Cloning and Expression of the Neonatal Rat Intestinal Fc Receptor, a Major Histocompatability Complex Class I Antigen Homolog.
(C) JOURNAL: Cold Spring Harbor Symposia on Quantitative Biology
(D) VOLUME: 54
(E) ISSUE:
(F) PAGES: 571-580
(G) DATE: 1989
(H) DOCUMENT NUMBER:
(I) FILING DATE:
(J) PUBLICATION DATE:
(K) RELEVANT RESIDUES IN SEQ ID NO:1: FROM 1 TO 16

(xi) SEQUENCE DESCRIPTION: SEQ ID NO: 1:

| Ala | Glu | Pro | Arg | Leu | Pro | Leu | Met | Tyr | His | Leu | Ala | Ala | Val | Ser | Asp |
|---|---|---|---|---|---|---|---|---|---|---|---|---|---|---|---|
| 1 | | | | 5 | | | | | 10 | | | | | 15 | |

(2) INFORMATION FOR SEQ ID NO: 2:

(i) SEQUENCE CHARACTERISTICS:
(A) LENGTH: 16 amino acid residues
(B) TYPE: Amino acid
(C) STRANDEDNESS:
(D) TOPOLOGY: Linear (ii) MOLECULE TYPE: Protein/Peptide (iii) HYPOTHETICAL: No (iv) ANTI-SENSE:

(v) FRAGMENT TYPE: N-terminal (vi) ORIGINAL SOURCE:
(A) ORGANISM: Rattus norvegious
(B) STRAIN: Sprague-Dawley
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:

(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY: This sequence contains the first 16 amino acids of the mature protein rat beta 2-microhlobulin.
(B) LOCATION: Rat beta 2- microglobulin (a.a. 1 to 16) from 1 to 16.
(C) IDENTIFICATION METHOD: Purified, soluble FcRn was subjected to N-terminal sequence analysis.
(D) OTHER INFORMATION: This sequence was determined to verify that the secreted, soluble FcRn heterodimer consisted of FcRn heavy chain and rat beta 2-microhlobulin at a stoichiometry of 1:1.

(x) PUBLICATION INFORMATION:
(A) AUTHORS: Sundelin, J.
              Bjorck, L.
              Logdberg, L.
(B) TITLE: The Complete Amino Acid Sequence of Rat beta 2- Microglobulin.
(C) JOURNAL: Scand. J. Immunol.
(D) VOLUME: 27
(E) ISSUE:
(F) PAGES: 195-199
(G) DATE: 1988
(H) DOCUMENT NUMBER:
(I) FILING DATE:
(J) PUBLICATION DATE:
(K) RELEVANT RESIDUES IN SEQ ID NO:2: FROM 1 TO 16

(xi) SEQUENCE DESCRIPTION: SEQ ID NO: 2:

Ile Gln Lys Thr Pro Gln Ile Gln Val Tyr Ser Arg His Pro Pro Glu
1               5                   10                  15

(2) INFORMATION FOR SEQ ID NO: 3:

(i) SEQUENCE CHARACTERISTICS:
(A) LENGTH: 14 amino acids
(B) TYPE: Amino acid
(C) STRANDEDNESS:
(D) TOPOLOGY: Linear (ii) MOLECULE TYPE: Protein/Peptide (iii) HYPOTHETICAL: No (iv) ANTI-SENSE:

(v) FRAGMENT TYPE: Internal fragment (vi) ORIGINAL SOURCE:
(A) ORGANISM: Rattus norvegious
(B) STRAIN:
(C) INDIVIDUAL ISOLATE:
(D) DEVELOPMENTAL STAGE: 11 day- old/germ-line
(E) HAPLOTYPE:
(F) TISSUE TYPE: Proximal third of small intestine
(G) CELL TYPE: Epithelial cells
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY: A 14 amino acid internal fragment of the wild-type FcRn heavy chain.
        ( B ) LOCATION: FcRn heavy chain (a.a. 265 to 278) from 1 to 14.
        ( C ) IDENTIFICATION METHOD: Sequence as reported by N.E.
                Simister and K.E. Mostov in Nature 337, 184-187 (1989).
        ( D ) OTHER INFORMATION: This wild- type sequence was referenced
                so that the reader could compare the modified FcRn heavy
                chain sequences to that of the wild-type.

( x ) PUBLICATION INFORMATION:
            ( A ) AUTHORS: Simister, N.E.
                    Mostov, K.E.
            ( B ) TITLE: An Fc receptor structurally related to MHC class I
                    antigens.
            ( C ) JOURNAL: Nature
            ( D ) VOLUME: 337
            ( E ) ISSUE:
            ( F ) PAGES: 184-187
            ( G ) DATE: 12-Jan-1989
            ( H ) DOCUMENT NUMBER:
            ( I ) FILING DATE:
            ( J ) PUBLICATION DATE:
            ( K ) RELEVANT RESIDUES IN SEQ ID NO:3: FROM 1 TO 16.

( x ) PUBLICATION INFORMATION:
            ( A ) AUTHORS: Simister, N.E.
                    Mostov, K.E.
            ( B ) TITLE: Cloning and Expression of the Neonatal Rat
                    Intestinal Fc Receptor, a Major Histocompatability
                    Complex Class I Antigen Homolog.
            ( C ) JOURNAL: Cold Spring Harbor Symposia on Quantitative
                    Biology
            ( D ) VOLUME: 54
            ( E ) ISSUE:
            ( F ) PAGES: 571-580
            ( G ) DATE: 1989
            ( H ) DOCUMENT NUMBER:
            ( I ) FILING DATE:
            ( J ) PUBLICATION DATE:
            ( K ) RELEVANT RESIDUES IN SEQ ID NO:3: FROM 1 TO 14

( x i ) SEQUENCE DESCRIPTION: SEQ ID NO: 3:

Leu  Thr  Val  Asp  Leu  Asp  Ser  Pro  Ala  Arg  Ser  Ser  Val  Pro
1                  5                        10

( 2 ) INFORMATION FOR SEQ ID NO: 4:

( i ) SEQUENCE CHARACTERISTICS:
                ( A ) LENGTH: 42 amino acid residues
                ( B ) TYPE: Amino acid
                ( C ) STRANDEDNESS:
                ( D ) TOPOLOGY: Linear ( i i ) MOLECULE TYPE: Protein/Peptide ( i i i ) HYPOTHETICAL: No ( i v ) ANTI-SENSE:

( v ) FRAGMENT TYPE: C-terminal fragment ( v i ) ORIGINAL SOURCE:
                ( A ) ORGANISM: FcRn from Rattus norvegicus DAF from Homo
                        spaiens
                ( B ) STRAIN:
                ( C ) INDIVIDUAL ISOLATE:
                ( D ) DEVELOPMENTAL STAGE: FcRn from 11 day old/germ-line
                ( E ) HAPLOTYPE:
                ( F ) TISSUE TYPE: FcRn from proximal third of small intestine
                ( G ) CELL TYPE: FcRn from epithelial cells
                ( H ) CELL LINE: DAF from HeLa cells
                ( I ) ORGANELLE:

( v i i ) IMMEDIATE SOURCE:
                ( A ) LIBRARY:
                ( B ) CLONE: 'p-51-DAF' cell line produces chimeric FcRn heavy
                        chain with the C-terminus given in SEQ ID NO. 4. This
                        C-terminus is modified intracellularly, providing
                        covalent lipid attachment.

(viii) POSITION IN GENOME:
  (A) CHROMOSOME/SEGMENT:
  (B) MAP POSITION:
  (C) UNITS:

(ix) FEATURE:
  (A) NAME/KEY: The insertion of the DAF amino acid sequence after the FcRn heavy chain alpha-3 domain but before the transmembrane domain yields a functional, lipid-linked FcRn heavy chain.
  (B) LOCATION: FcRn heavy chain (a.a. 265 to 269) from 1 to 5, DAF (a.a. 311 to 347) from 6 to 42.
  (C) IDENTIFICATION METHOD: The cell surface expression of lipid- linked FcRn heavy chain was confirmed by immunostaining. Experiments proved that it retained its physiological, pH-dependent binding of immunoglobulin Fc.
  (D) OTHER INFORMATION: Intracellular modification results in the removal of sequence C-terminal of residue 25 and the anchoring of the protein in the cell membrane by the attachment of a phospholipid to the protein's C-terminal region.

(x) PUBLICATION INFORMATION:
  (A) AUTHORS: Gastinel, Louis N.
      Simister, N.E.
      Bjorkman, P.J.
  (B) TITLE: Expression and Crystallization of a Soluble and Functional form of a Fc Receptor Related to Class I Histocompatibility Molecules.
  (C) JOURNAL: Proc. Natl. Acad. Sci. U.S.A.
  (D) VOLUME: 89
  (E) ISSUE:
  (F) PAGES: 638-642
  (G) DATE:
  (H) DOCUMENT NUMBER:
  (I) FILING DATE:
  (J) PUBLICATION DATE:
  (K) RELEVANT RESIDUES IN SEQ ID NO:4: FROM 1 TO 42

(xi) SEQUENCE DESCRIPTION: SEQ ID NO: 4:

```
Leu Thr Val Asp Leu Pro Asn Lys Gly Ser Gly Thr Thr Ser Gly Thr
1               5                   10                  15

Thr Arg Leu Leu Ser Gly His Thr Cys Phe Thr Leu Thr Gly Leu Leu
            20                  25                  30

Gly Thr Leu Val Thr Met Gly Leu Leu Thr
        35                  40
```

(2) INFORMATION FOR SEQ ID NO: 5:

(i) SEQUENCE CHARACTERISTICS:
      (A) LENGTH: 5 amino acids
      (B) TYPE: Amino acid
      (C) STRANDEDNESS:
      (D) TOPOLOGY: Linear (ii) MOLECULE TYPE: Protein/Peptide (iii) HYPOTHETICAL: No (iv) ANTI-SENSE:

(v) FRAGMENT TYPE: C-terminal (vi) ORIGINAL SOURCE:
      (A) ORGANISM: Rattus norvegious
      (B) STRAIN: Wistar
      (C) INDIVIDUAL ISOLATE:
      (D) DEVELOPMENTAL STAGE: 11 day old/germ line
      (E) HAPLOTYPE:
      (F) TISSUE TYPE: Proximal third of small intestine
      (G) CELL TYPE: Epithelial cells
      (H) CELL LINE:
      (I) ORGANELLE:

(vii) IMMEDIATE SOURCE:

( A ) LIBRARY:
                    ( B ) CLONE: 'p51-stop' cell line produces FcRn heavy chain with
                         the C- terminus given in SEQ ID NO: 5.

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY: The insertion of a stop-codon 3' of the codon
                         for FcRn heavy chain amino acid residue 269 results in
                         the synthesis of an FcRn heavy chain that has amino acid
                         269 as its C- terminal residue.
                    ( B ) LOCATION: FcRn heavy chain (a.a. 265 to 269) from 1 to 5.
                    ( C ) IDENTIFICATION METHOD: The production of a soluble FcRn
                         heavy chain implied that the new stop codon had
                         effectively terminated the synthesis of heavy chain
                         at amino acid 269.
                    ( D ) OTHER INFORMATION: The truncated FcRn heavy chain
                         (C - t e r m i n a l   r e s i d u e   =   a . a .   2 6 9 ) can form water soluble
                         FcRn heterodimer (with rat beta 2-microglobulin) that
                         retains its physiological pH dependent binding of IgG
                         Fc regions.

( x ) PUBLICATION INFORMATION:
                    ( A ) AUTHORS: Gastinel, Louis N.
                         Simister, N.E.
                         Bjorkman, P.J.
                    ( B ) TITLE: Expression and Crystallization of a Soluble and
                         Functional form of an Fc Receptor Related to Class I
                         Histocompatibility Molecules
                    ( C ) JOURNAL: Proc. Natl. Acad. Sci. U.S.A.
                    ( D ) VOLUME: 89
                    ( E ) ISSUE:
                    ( F ) PAGES: 638-642
                    ( G ) DATE:
                    ( H ) DOCUMENT NUMBER:
                    ( I ) FILING DATE:
                    ( J ) PUBLICATION DATE: 15-Jan- 1992
                    ( K ) RELEVANT RESIDUES IN SEQ ID NO:5: FROM 1 TO 5

( x i ) SEQUENCE DESCRIPTION: SEQ ID NO: 5:

Leu  Thr  Val  Asp  Leu
1                   5

( 2 ) INFORMATION FOR SEQ ID NO: 6:

( i ) SEQUENCE CHARACTERISTICS:
                    ( A ) LENGTH: 5 amino acid residues
                    ( B ) TYPE: Amino acid
                    ( C ) STRANDEDNESS:
                    ( D ) TOPOLOGY: Linear ( i i ) MOLECULE TYPE: Protein/Peptide ( i i i ) HYPOTHETICAL: No ( i v ) ANTI-SENSE:

( v ) FRAGMENT TYPE: C-terminal ( v i ) ORIGINAL SOURCE:
                    ( A ) ORGANISM: Rattus norvegious
                    ( B ) STRAIN: Sprague-Dawley
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:

(A) CHROMOSOME/SEGMENT:
                    (B) MAP POSITION:
                    (C) UNITS:

(ix) FEATURE:
                    (A) NAME/KEY: A 5 amino acid, C- terminal fragment of wild-
                            type rat beta 2-microglobulin.
                    (B) LOCATION: Rat beta 2- microglobulin (a.a. 95 to 99) from
                            1 to 5.
                    (C) IDENTIFICATION METHOD: Sequence is that reported by
                            Sundelin, J. et al., in the Scand. J. Immunol., Vol. 27,
                            pp. 195-199 (1988).
                    (D) OTHER INFORMATION: This wild- type sequence was referenced
                            so that the reader should compare the modified beta
                            2- microglobulin sequences to that of the wild-type.

(x) PUBLICATION INFORMATION:
                    (A) AUTHORS: Sundelin, J.
                            Bjorck, L.
                            Logdberg, L.
                    (B) TITLE: The Complete Amino Acid Sequence of Rat beta
                            2- Microglobulin.
                    (C) JOURNAL: Scand. J. Immunol.
                    (D) VOLUME: 27
                    (E) ISSUE:
                    (F) PAGES: 195-199
                    (G) DATE: 1988
                    (H) DOCUMENT NUMBER:
                    (I) FILING DATE:
                    (J) PUBLICATION DATE:
                    (K) RELEVANT RESIDUES IN SEQ ID NO:6: FROM 1 TO 5

(xi) SEQUENCE DESCRIPTION: SEQ ID NO: 6:

Trp  Asp  Arg  Asp  Met
1                    5

(2) INFORMATION FOR SEQ ID NO: 7:

(i) SEQUENCE CHARACTERISTICS:
                    (A) LENGTH: 42 amino acid residues
                    (B) TYPE: Amino acid
                    (C) STRANDEDNESS:
                    (D) TOPOLOGY: Linear (ii) MOLECULE TYPE: Protein/Peptide (iii) HYPOTHETICAL: No (iv) ANTI-SENSE:

(v) FRAGMENT TYPE: C-terminal (vi) ORIGINAL SOURCE:
                    (A) ORGANISM: Beta 2-M from Rattus norvegious DAF from Homo
                            sapiens
                    (B) STRAIN: Beta 2-M from Sprague- Dawley
                    (C) INDIVIDUAL ISOLATE:
                    (D) DEVELOPMENTAL STAGE:
                    (E) HAPLOTYPE:
                    (F) TISSUE TYPE:
                    (G) CELL TYPE:
                    (H) CELL LINE: DAF from HeLa cells
                    (I) ORGANELLE:

(vii) IMMEDIATE SOURCE:
                    (A) LIBRARY:
                    (B) CLONE: Beta 2m-DAF' cell line produces chimeric rat beta
                            2- microglobulin with the C-terminus given in SEQ ID NO:
                            7. This C- terminus is modified intracellularly providing
                            covalent lipid attachment.

(viii) POSITION IN GENOME:
                    (A) CHROMOSOME/SEGMENT:
                    (B) MAP POSITION:
                    (C) UNITS:

(ix) FEATURE:
                    (A) NAME/KEY: The insertion of the DAF amino acid sequence after the C- terminal residue of rat beta 2-microglobulin
results in the synthesis of a functional, lipid-linked
beta 2- microglobulin.
- ( B ) LOCATION: Rat beta 2- microglobulin (a.a. 95 to 99) from
1 to 5 DAF (a.a. 311 to 347) from 6 to 42.
- ( C ) IDENTIFICATION METHOD: The cell surface expression of
lipid- linked rat beta 2-microploblin was confirmed by
imunostaining.
- ( D ) OTHER INFORMATION: Intracellular modification results in
the removal of sequence C-terminal of residue 25 and the
anchoring of the protein in the cell membrane by
attachment of a phospholipid to the protein's C-terminal
region.

( x ) PUBLICATION INFORMATION:
- ( A ) AUTHORS: Gastinel, Louis N.
Simister, N.E.
Bjorkman, P.J.
- ( B ) TITLE: Expression and Crystallization of a Soluble and
Functional form of a Fc Receptor Related to Class I
Histocompatibility Molecules.
- ( C ) JOURNAL: Proc. Natl. Acad. Sci. U.S.A.
- ( D ) VOLUME: 89
- ( E ) ISSUE:
- ( F ) PAGES: 638-642
- ( G ) DATE:
- ( H ) DOCUMENT NUMBER:
- ( I ) FILING DATE:
- ( J ) PUBLICATION DATE: 16-Jan- 1992
- ( K ) RELEVANT RESIDUES IN SEQ ID NO:7: FROM 1 TO 42

( x i ) SEQUENCE DESCRIPTION: SEQ ID NO: 7:

```
Trp Asp Arg Asp Met Pro Asn Lys Gly Ser Gly Thr Thr Ser Gly Thr
 1               5                  10                  15

Thr Arg Leu Leu Ser Gly His Thr Cys Phe Thr Leu Thr Gly Leu Leu
             20                  25                  30

Gly Thr Leu Val Thr Met Gly Leu Leu Thr
             35                  40
```

( 2 ) INFORMATION FOR SEQ ID NO: 8:

- ( i ) SEQUENCE CHARACTERISTICS:
  - ( A ) LENGTH: 366 amino acid residues
  - ( B ) TYPE: Amino acid
  - ( C ) STRANDEDNESS:
  - ( D ) TOPOLOGY: Linear

- ( x ) PUBLICATION INFORMATION:
  - ( A ) AUTHORS: Simister, N.E.
Mostov, K.E.
  - ( B ) TITLE: An Fc receptor structurally related to MHC class I
antigens.
  - ( C ) JOURNAL: Nature
  - ( D ) VOLUME: 337
  - ( E ) ISSUE:
  - ( F ) PAGES: 184-187
  - ( G ) DATE: 12-Jan-19891989
  - ( H ) DOCUMENT NUMBER:
  - ( I ) FILING DATE:
  - ( J ) PUBLICATION DATE:
  - ( K ) RELEVANT RESIDUES IN SEQ ID NO:8: FROM -22 TO 344

( x i ) SEQUENCE DESCRIPTION: SEQ ID NO: 8:

```
Met Gly Met Ser Gln Pro Gly Val Leu Leu Ser Leu Leu Leu Val Leu
-22       -20                 -15                 -10

Leu Pro Gln Thr Trp Gly Ala Glu Pro Arg Leu Pro Leu Met Tyr His
     -5              -1  +1               5                  10

Leu Ala Ala Val Ser Asp Leu Ser Thr Gly Leu Pro Ser Phe Trp Ala
                 15                  20                  25

Thr Gly Trp Leu Gly Ala Gln Gln Tyr Leu Thr Tyr Asn Asn Leu Arg
             30                  35                  40
```

|  |  |  |  |  |  |  |  |  |  |  |  |  |  |  |
|---|---|---|---|---|---|---|---|---|---|---|---|---|---|---|
| Gln | Glu | Ala | Asp | Pro | Cys | Gly | Ala | Trp | Ile | Trp | Glu | Asn | Gln | Val | Ser |
|  |  | 45 |  |  |  |  | 50 |  |  |  |  | 55 |  |  |  |
| Trp | Tyr | Trp | Glu | Lys | Glu | Thr | Thr | Asp | Leu | Lys | Ser | Lys | Glu | Gln | Leu |
|  | 60 |  |  |  |  | 65 |  |  |  |  | 70 |  |  |  |  |
| Phe | Leu | Glu | Ala | Ile | Arg | Thr | Leu | Glu | Asn | Gln | Ile | Asn | Gly | Thr | Phe |
| 75 |  |  |  |  | 80 |  |  |  |  | 85 |  |  |  |  | 90 |
| Thr | Leu | Gln | Gly | Leu | Leu | Gly | Cys | Glu | Leu | Ala | Pro | Asp | Asn | Ser | Ser |
|  |  |  |  | 95 |  |  |  |  | 100 |  |  |  |  | 105 |  |
| Leu | Pro | Thr | Ala | Val | Phe | Ala | Leu | Asn | Gly | Glu | Glu | Phe | Met | Arg | Phe |
|  |  |  | 110 |  |  |  |  | 115 |  |  |  |  | 120 |  |  |
| Asn | Pro | Arg | Thr | Gly | Asn | Trp | Ser | Gly | Glu | Trp | Pro | Glu | Thr | Asp | Ile |
|  |  | 125 |  |  |  |  | 130 |  |  |  |  | 135 |  |  |  |
| Val | Gly | Asn | Leu | Trp | Met | Lys | Gln | Pro | Glu | Ala | Ala | Arg | Lys | Glu | Ser |
|  | 140 |  |  |  |  | 145 |  |  |  |  | 150 |  |  |  |  |
| Glu | Phe | Leu | Leu | Thr | Ser | Cys | Pro | Glu | Arg | Leu | Leu | Gly | His | Leu | Glu |
| 155 |  |  |  |  | 160 |  |  |  |  | 165 |  |  |  |  | 170 |
| Arg | Gly | Arg | Gln | Asn | Leu | Glu | Trp | Lys | Glu | Pro | Pro | Ser | Met | Arg | Leu |
|  |  |  |  | 175 |  |  |  |  | 180 |  |  |  |  | 185 |  |
| Lys | Ala | Arg | Pro | Gly | Asn | Ser | Gly | Ser | Ser | Val | Leu | Thr | Cys | Ala | Ala |
|  |  |  | 190 |  |  |  |  | 195 |  |  |  |  | 200 |  |  |
| Phe | Ser | Phe | Tyr | Pro | Pro | Glu | Leu | Lys | Phe | Arg | Phe | Leu | Arg | Asn | Gly |
|  |  | 205 |  |  |  |  | 210 |  |  |  |  | 215 |  |  |  |
| Leu | Ala | Ser | Gly | Ser | Gly | Asn | Cys | Ser | Thr | Gly | Pro | Asn | Gly | Asp | Gly |
|  | 220 |  |  |  |  | 225 |  |  |  |  | 230 |  |  |  |  |
| Ser | Phe | His | Ala | Trp | Ser | Leu | Leu | Glu | Val | Lys | Arg | Gly | Asp | Glu | His |
| 235 |  |  |  |  | 240 |  |  |  |  | 245 |  |  |  |  | 250 |
| His | Tyr | Gln | Cys | Gln | Val | Glu | His | Glu | Gly | Leu | Ala | Gln | Pro | Leu | Thr |
|  |  |  |  | 255 |  |  |  |  | 260 |  |  |  |  | 265 |  |
| Val | Asp | Leu | Asp | Ser | Pro | Ala | Arg | Ser | Ser | Val | Pro | Val | Val | Gly | Ile |
|  |  |  | 270 |  |  |  |  | 275 |  |  |  |  | 280 |  |  |
| Ile | Leu | Gly | Leu | Leu | Leu | Val | Val | Val | Ala | Ile | Ala | Gly | Gly | Val | Leu |
|  |  | 285 |  |  |  |  | 290 |  |  |  |  | 295 |  |  |  |
| Leu | Trp | Asn | Arg | Met | Arg | Ser | Gly | Leu | Pro | Ala | Pro | Trp | Leu | Ser | Leu |
|  | 300 |  |  |  |  | 305 |  |  |  |  | 310 |  |  |  |  |
| Ser | Gly | Asp | Asp | Ser | Gly | Asp | Leu | Leu | Pro | Gly | Gly | Asn | Leu | Pro | Pro |
| 315 |  |  |  |  | 320 |  |  |  |  | 325 |  |  |  |  | 330 |
| Glu | Ala | Glu | Pro | Gln | Gly | Val | Asn | Ala | Phe | Pro | Ala | Thr | Ser |  |  |
|  |  |  |  | 335 |  |  |  |  | 340 |  |  |  | 344 |  |  |

( 2 ) INFORMATION FOR SEQ ID NO: 9:

( i ) SEQUENCE CHARACTERISTICS:
        ( A ) LENGTH: 99 amino acid residues
        ( B ) TYPE: Amino acid
        ( C ) STRANDEDNESS:
        ( D ) TOPOLOGY: Linear ( x ) PUBLICATION INFORMATION:
        ( A ) AUTHORS: Sundelin, J.
                Bjorck, L.
                Logdberg, L.
        ( B ) TITLE: The Complete Amino Acid Sequence of Rat beta
             2- Microglobulin
        ( C ) JOURNAL: Scand. J. Immunol.
        ( D ) VOLUME: 27
        ( E ) ISSUE:
        ( F ) PAGES: 195-199
        ( G ) DATE: 1988
        ( H ) DOCUMENT NUMBER:
        ( I ) FILING DATE:
        ( J ) PUBLICATION DATE:

(K) RELEVANT RESIDUES IN SEQ ID NO:9: FROM 1 TO 99

(xi) SEQUENCE DESCRIPTION: SEQ ID NO: 9:

```
Ile Gln Lys Thr Pro Gln Ile Gln Val Tyr Ser Arg His Pro Pro Glu
 1               5                   10                  15
Asn Gly Lys Pro Asn Phe Leu Asn Cys Tyr Val Ser Gln Phe His Pro
            20                  25                  30
Pro Gln Ile Glu Ile Glu Leu Leu Lys Asn Gly Lys Lys Ile Pro Asn
        35                  40                  45
Ile Glu Met Ser Asp Leu Ser Phe Ser Lys Asp Trp Ser Phe Tyr Ile
    50                  55                  60
Leu Ala His Thr Glu Phe Thr Pro Thr Glu Thr Asp Val Tyr Ala Cys
65                  70                  75                  80
Arg Val Lys His Val Thr Lys Leu Glu Pro Lys Thr Val Thr Trp Asp
                85                  90                  95
Arg Asp Met
        99
```

What is claimed is:

1. A soluble heterodimeric Fc receptor comprising a $\beta_2$-microglobulin light chain, and a heavy chain derived from a mammalian, membrane-bound Fc receptor by truncating said membrane-bound Fc receptor heavy chain to include only extracellular domains, said soluble Fc receptor having pH-determinable binding capability for the Fc portion of at least one antibody or a complex of said antibody, wherein said soluble, mammal-derived Fc receptor is capable of binding to said antibody over a pH ranging from about 5.5 to about 6.5 and releasing said antibody over a pH ranging from about 7.5 to about 8.5.

2. The soluble heterodimeric Fc receptor of claim 1, wherein said soluble Fc receptor essentially exhibits the antibody-binding capabilities of the membrane-bound Fc receptor from which said soluble Fc receptor has been derived.

3. The soluble heterodimeric Fc receptor of claim 1, wherein said truncated heavy chain is derived from a membrane-bound Fc receptor of the kind expressed on the apical surface of intestinal epithelial cells of mammals during the first few weeks of life.

4. The soluble heterodimeric Fc receptor of claim 1, wherein both said $\beta_2$-microglobulin light chain and said truncated heavy chain are derived from the same species of mammal.

5. The soluble heterodimeric Fc receptor of claim 4, wherein said truncated heavy chain is derived from rat membrane-bound Fc receptor.

6. The soluble heterodimeric Fc receptor of claim 5, wherein a sequence of said truncated heavy chain comprises Ala Glu Pro Arg Leu Pro Leu Met Tyr His Leu Ala Ala Val Ser Asp.

7. The soluble heterodimeric Fc receptor of claim 5, wherein a sequence of said $\beta_2$-microglobulin chain comprises Ile Gln Lys Thr Pro Gln Ile Gln Val Tyr Ser Arg His Pro Pro Glu.

* * * * *